United States Patent [19]

Voda

[11] Patent Number: 5,445,625
[45] Date of Patent: Aug. 29, 1995

[54] ANGIOPLASTY GUIDE CATHETER

[76] Inventor: Jan Voda, 1404 Camden Way, Oklahoma City, Okla. 73116

[21] Appl. No.: 259,567

[22] Filed: Jun. 14, 1994

Related U.S. Application Data

[63] Continuation of Ser. No. 969,891, Oct. 30, 1992, abandoned, Continuation-in-part of Ser. No. 622,873, Jan. 23, 1991, abandoned.

[51] Int. Cl.⁶ ............................................. A61M 25/00
[52] U.S. Cl. ...................................... 604/281; 604/280
[58] Field of Search ............ 604/95, 96, 264, 281–282; 606/194; 128/656–658, 772

[56] References Cited

U.S. PATENT DOCUMENTS

| | | | |
|---|---|---|---|
| 3,935,857 | 2/1976 | Co | 128/2.05 |
| 3,938,501 | 2/1976 | Erikson | 128/2 A |
| 4,020,829 | 5/1977 | Willson et al. | 128/2 M |
| 4,033,331 | 7/1977 | Guss et al. | 128/2 M |
| 4,117,836 | 10/1978 | Erikson | 128/2.05 R |
| 4,169,464 | 10/1979 | Obrez | 128/657 |
| 4,195,637 | 4/1980 | Gruntzig et al. | 128/348 |
| 4,292,976 | 10/1981 | Banka | 128/656 |
| 4,430,083 | 2/1984 | Ganz et al. | 604/283 |
| 4,547,193 | 10/1985 | Rydell | 604/282 |
| 4,551,292 | 11/1985 | Fletcher et al. | 264/139 |
| 4,563,181 | 1/1986 | Wijayarathna et al. | 604/280 |
| 4,568,338 | 2/1986 | Todd | 604/281 |
| 4,733,669 | 3/1988 | Segal | 128/663 |
| 4,738,667 | 4/1988 | Galloway . | |
| 4,747,840 | 5/1988 | Ladika et al. | 604/281 |
| 4,781,682 | 11/1988 | Patel | 604/96 |
| 4,784,639 | 11/1988 | Patel | 604/53 |
| 4,790,831 | 12/1988 | Skribiski | 604/282 |
| 4,813,930 | 3/1989 | Elliott | 604/53 |
| 4,820,349 | 4/1989 | Saab | 128/344 |
| 4,822,345 | 4/1989 | Danforth | 604/282 |
| 4,867,174 | 9/1989 | Skribiski | 128/772 |
| 4,882,777 | 11/1989 | Narula . | |
| 4,883,058 | 11/1989 | Ruiz | 128/654 |
| 4,886,506 | 12/1989 | Lovgren et al. | 604/280 |
| 4,898,577 | 2/1990 | Badger et al. . | |
| 4,898,591 | 2/1990 | Jang et al. | 604/282 |
| 4,909,787 | 3/1990 | Danforth | 604/95 |
| 4,925,445 | 5/1990 | Sakamoto et al. . | |
| 4,935,004 | 6/1990 | Cruz . | |
| 4,935,017 | 6/1990 | Sylvanowicz . | |
| 4,950,228 | 8/1990 | Knapp, Jr. et al. . | |
| 4,976,691 | 12/1990 | Sahota | 604/96 |
| 4,981,477 | 1/1991 | Schon et al. . | |
| 4,983,166 | 1/1991 | Yamawaki | 604/96 |
| 4,994,032 | 2/1991 | Sugiyama et al. | 604/96 |
| 5,000,743 | 3/1991 | Patel | 606/194 |
| 5,035,686 | 7/1991 | Crittenden et al. | 604/96 |

(List continued on next page.)

FOREIGN PATENT DOCUMENTS

0132344A2  1/1985  European Pat. Off. .
0277366A1  8/1988  European Pat. Off. .

OTHER PUBLICATIONS

Mallinckrodt "Diagnostic Catheters" brochure Oct. 1990.

(List continued on next page.)

Primary Examiner—C. Fred Rosenbaum
Assistant Examiner—Mark Bockelman
Attorney, Agent, or Firm—Nawrocki, Rooney & Sivertson

[57] ABSTRACT

An angioplasty guide catheter adapted for use within a cardiovascular system and cooperable with a left main coronary artery. The guide catheter has a distal end portion such that with a distal tip of the distal end portion coaxially intubated within an ostium of the left main coronary artery fully disposed within the cardiovascular system, a portion of the distal end portion rests against and is substantially contiguous with a wall of the ascending aorta. A distal end of the resting portion is substantially directly opposite the ostium of the left main coronary artery and a portion of the distal end portion defines a generally rectilinear axis of support extending from the distal end of the resting portion across the ascending aorta to the ostium of the left main coronary artery.

7 Claims, 13 Drawing Sheets

U.S. PATENT DOCUMENTS

| | | | |
|---|---|---|---|
| 5,044,369 | 9/1991 | Sahota | 128/658 |
| 5,045,072 | 9/1991 | Castillo et al. | 604/280 |
| 5,058,595 | 10/1991 | Kern | 128/662 |
| 5,059,197 | 10/1991 | Urie et al. | 606/116 |
| 5,098,412 | 3/1992 | Shiu | 604/280 |
| 5,122,125 | 6/1992 | Deuss . | |
| 5,163,921 | 11/1992 | Feiring | 604/247 |
| 5,195,990 | 3/1993 | Weldon . | |
| 5,203,776 | 4/1993 | Durfee | 604/264 |

OTHER PUBLICATIONS

Bourassa "Cardiovascular Catheters Sterile" brochure Jun. 1972.

USCI "KIFA products" brochure pp. 1–12 Jun. 1974.

USCI "KIFA products" brochure pp. 1–7 1967.

"Coronary Arteriography and Angioplasty" Spencer B. King III, John S. Douglas pp. 182–238.

USCI Block TM Right Coronary Guiding Catheter, 1989, 2 pages.

USCI Video Tape ("Select Curve Guiding Catheter: Cannulating the Right coronary Artery") transcript and selected figures, 1988.

USCI Video Tape: *Select Curve Guiding Catheter: Cannulating the Right Coronary Artery,* USCI, C. R. Bard, 1988.

"Angled Tip of the Steerable Guidewire and Its Usefulness in Percutaneous Translumenal Coronary Angioplasty", Jan Voda, *Use of Angled Guidewires in PTCA,* 1987, pp. 204–210.

MediTech—Boston Scientific Corporation "Imager Angiographic Catheters" brochure Oct. 1990.

*U.S.C.I. Gruntzig Dilaca Coronary Dilatation Equipment,* U.S.C.I., C. R. Bard, Inc. 1990.

U.S.C.I. "Postirol II and Nycore TM Cardiovascular Catheter".

Arani STE: *A new catheter for angioplasty of the right coronary artery and aorta coronary bypass grafts,* Cath. Cardiovasc. Diag. 11:647–658, 1985.

Block, P. C. et al.: *PTCA in perspective,* U.S.C.I. Division, C. R. Bard, Inc. Billerica, Mass., pp. 23–41, 1986.

King S. B., III and Douglas S. Jr.: *Coronary Arteriography and Angioplasty,* McGraw–Hill, New York, Chapter 17, *Percutaneous Transluminal Coronary Angioplasty,* pp. 433–452, 1985.

Amplatz, K. et al., *Mechanics of Selective Coronary Artery Catheterization via Femoral Approach,* Radiology 89: 1040–1047, Jul. 1967.

Judkins, M., *Percutaneous Transfemoral Selective Coronary Arteriography,* Radiologic Clinics of North America—vol. VI, No. 3, Dec. 1968.

Carr, M., *The Use of the Guiding Catheter in Coronary Angioplastic: The Technique of Manipulating Catheters to Obtain the Necessary Power to Cross Tight Coronary Stenoses,* Catheterization and Cardiovascular Diagnosis 12: 189–197 (1986).

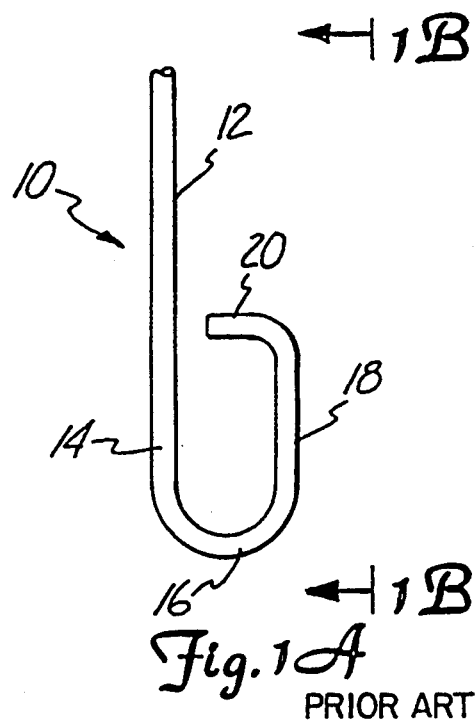
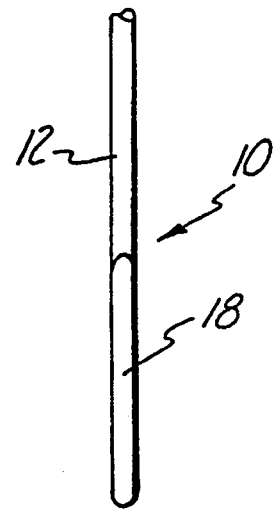
Fig. 1A PRIOR ART
Fig. 1B PRIOR ART
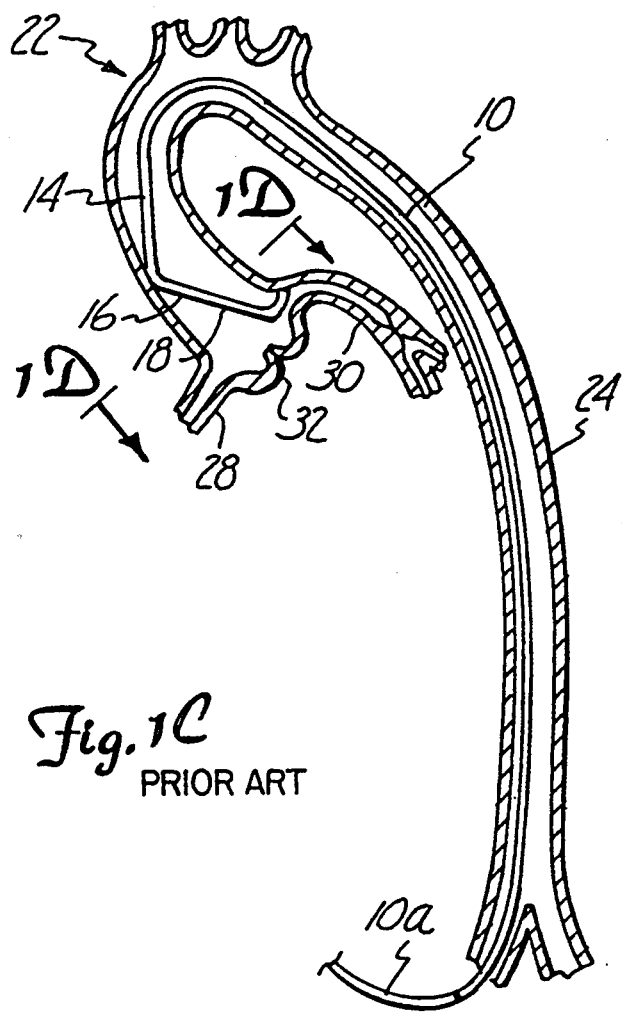
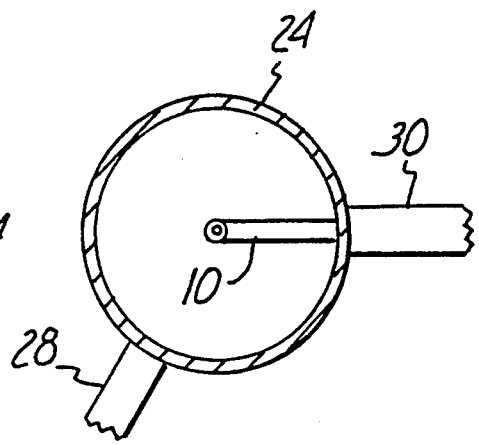
Fig. 1C PRIOR ART
Fig. 1D PRIOR ART

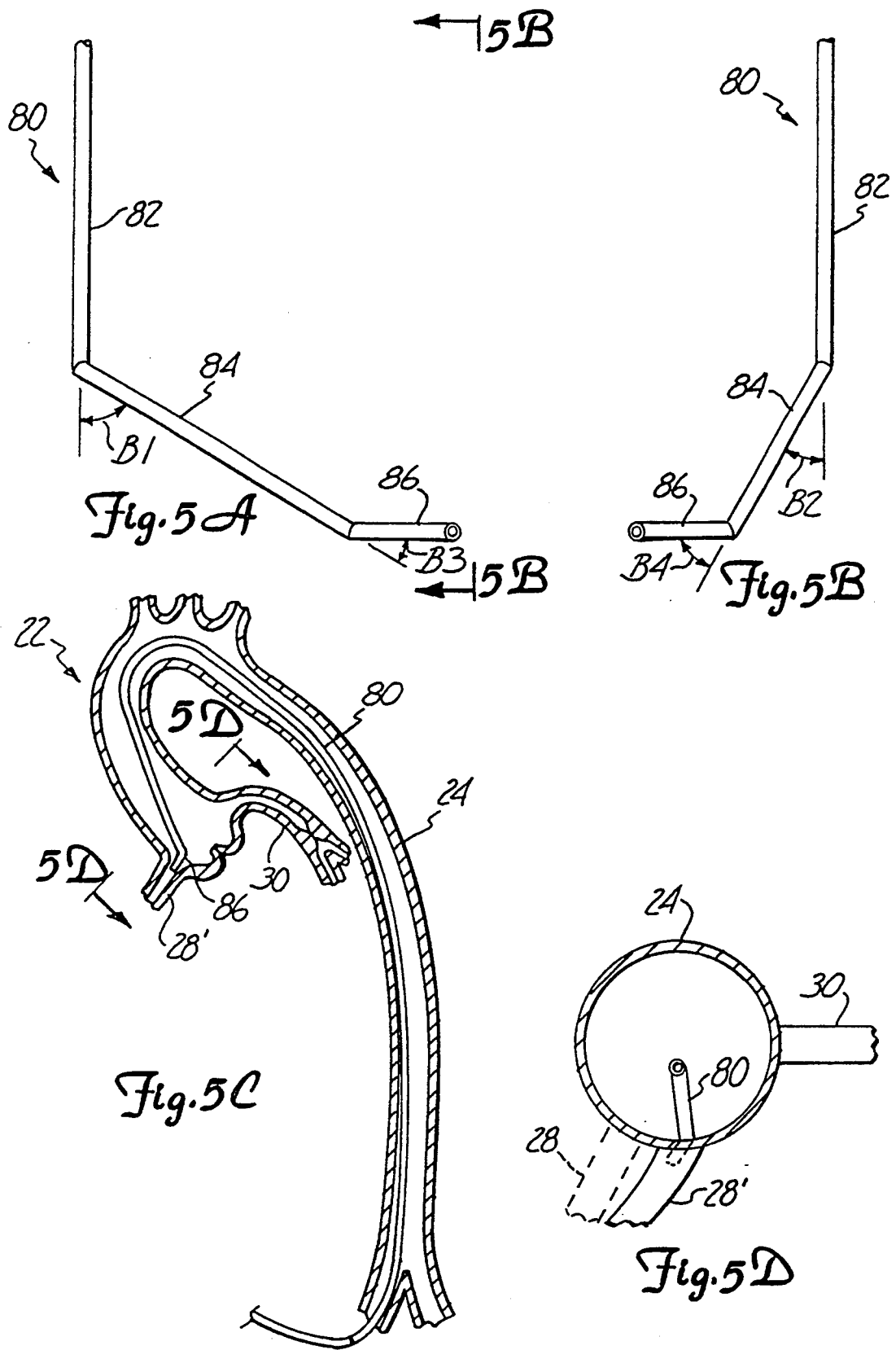

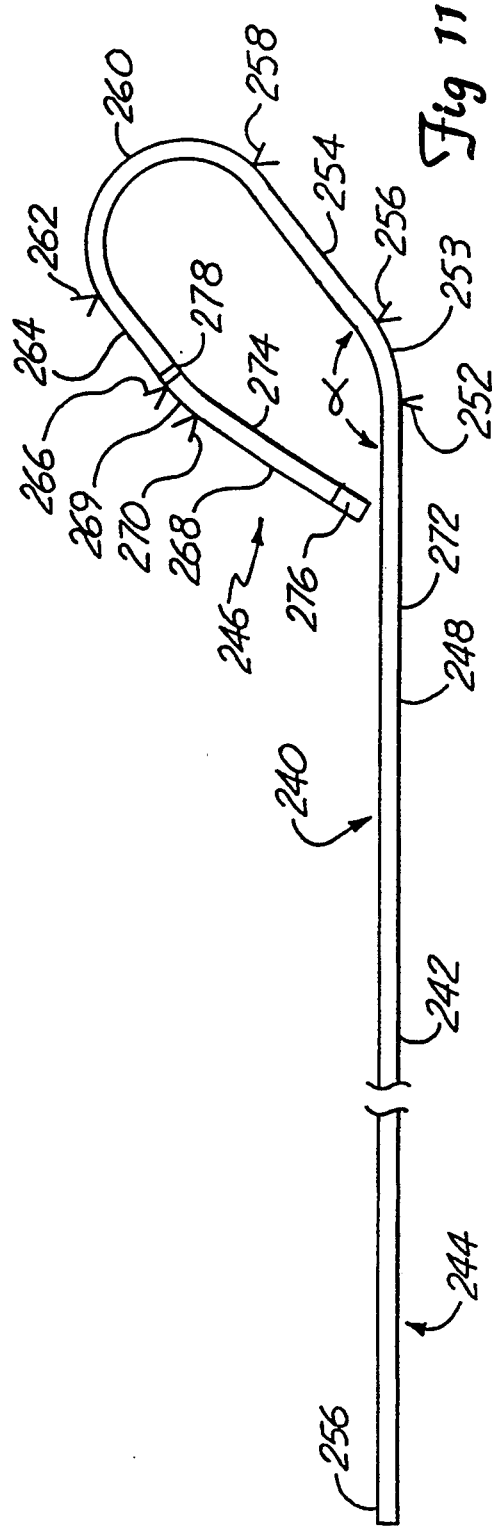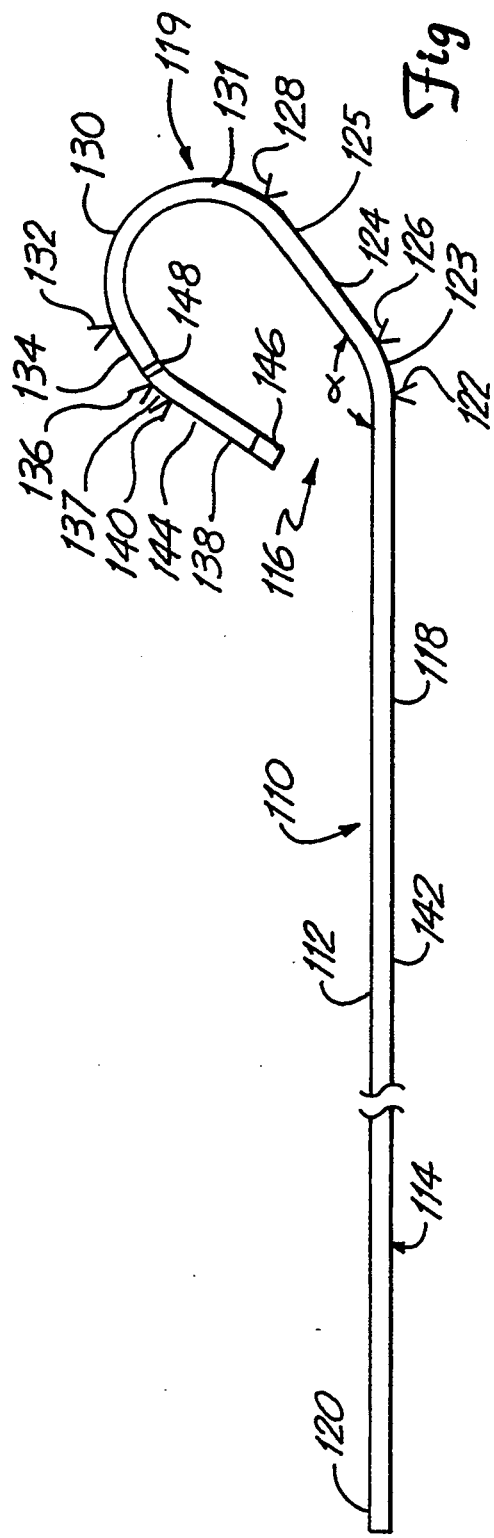

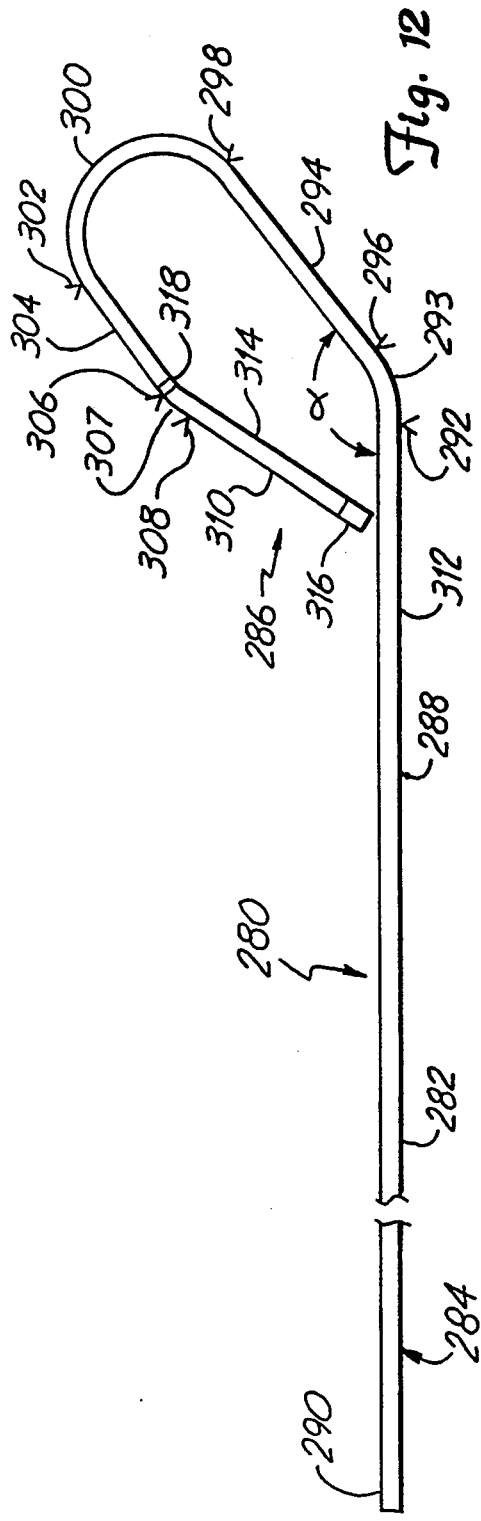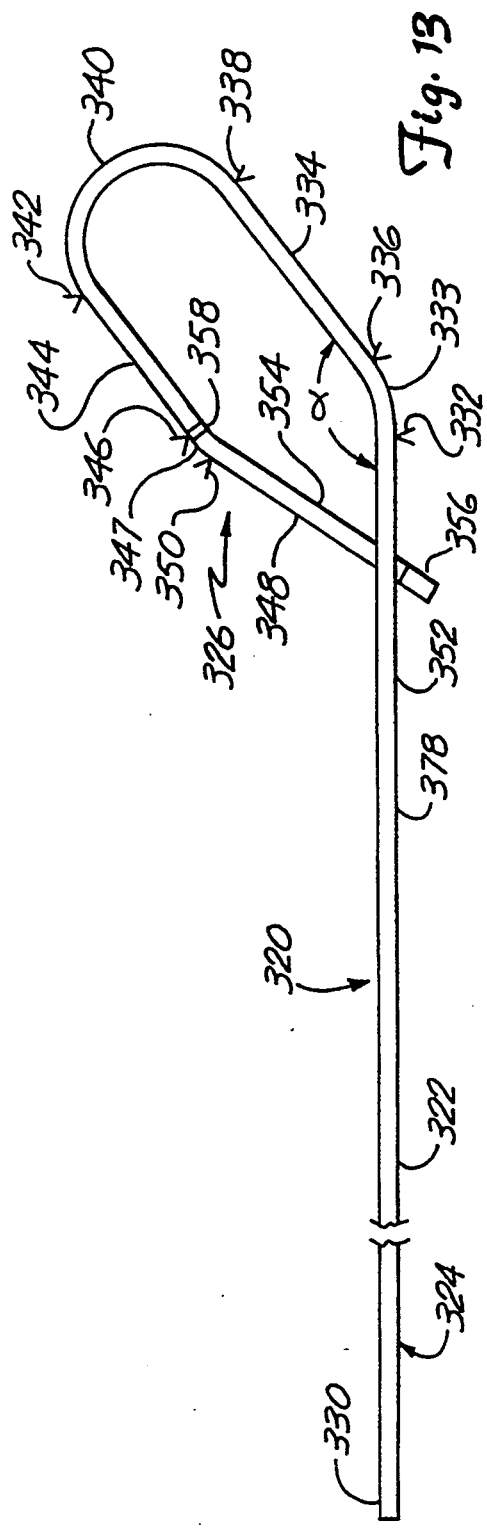

ANGIOPLASTY GUIDE CATHETER

This is a continuation of application Ser. No. 07/969,891 filed on Oct. 30, 1992 now abandoned which is a continuation-in-part of U.S. application Ser. No. 07/622,873, filed on Jan. 23, 1991 now abandoned, for GUIDE CATHETER CONSTRUCTION.

BACKGROUND OF THE INVENTION

This invention relates generally to catheters adapted to be inserted into the cardiovascular system of a living body and, more particularly, to an improved catheter having an improved distal end portion for more precise location in the particular artery of the cardiovascular system.

Catheters are often used in the performance of medical procedures such as coronary angiography for injecting dye, or the like, into the cardiovascular system for diagnosis; and angioplasty to widen the lumen of a coronary artery which has become at least partially blocked by a stenotic lesion causing an abnormal narrowing of the artery due to injury or disease. In these techniques the distal end of the catheter is introduced into the aorta by way of the femoral artery. The proximal end of the catheter is then manipulated so its distal end is inserted into the lumen of a selected coronary artery branching off from the aorta. A typical angioplasty procedure would involve initially inserting a guiding catheter into the cardiovascular system in the above manner, followed by a dilating catheter, a laser catheter, an atherectomy catheter, or the like, which is guided through the guiding catheter until its distal end portion is positioned within the stenotic lesion in the coronary artery to reduce the blockage in the artery. A diagnostic catheter would be used in the same manner.

The most common catheter used in treatment of the left coronary artery is what is often referred to as a "Judkins" catheter which has a specially shaped distal end portion for facilitating insertion into the artery. However, as will be specifically discussed, there are some disadvantages to the "Judkins" catheter, including its inability to align perfectly coaxially with selected artery and thus permit optimum treatment, and its inability to adequately support other devices such as balloon catheters. Also, the Judkins catheter forms relatively large angles when inserted into the cardiovascular system thus dissipating some of the axial forces transmitted through the catheter during use.

The Judkins-type catheter originally was designed and used for diagnostic angiography. However, with the advent of angioplasty, the Judkins-type catheter has been used routinely for about the last fourteen years to guide balloon catheters and other intravascular devices through the vasculature to the left main coronary artery. The overall shape/configuration of the Judkins-type catheter has remained basically the same throughout this period. Although some variations in its shape/configuration were made, the basic overall shape of the Judkins-type catheter has not been specifically adapted for the unique needs dictated by angioplasty procedures. Instead, the Judkins-type catheter (as commonly used in a left femoral approach technique for intubating the left main coronary artery) has been adapted only slightly from its original configuration that was designed for diagnostic angiographic procedures.

Accordingly, the Judkins-type catheter presents several difficulties when used for angioplasty procedures. Significantly, the principle problem associated with the use of a Judkins-type catheter as a guiding catheter is the lack of backup support which results in several undesirable consequences. When a Judkins-type guide catheter is disposed in the cardiovascular system and one attempts to push the balloon catheter distally across a tight stenosis, a resultant (opposite proximal) force is generated by the balloon catheter against the guide catheter. This problem is described in depth in Danforth U.S. Pat. No. 4,909,787. The result is that the tip of the Judkins-type catheter may become dislodged from the ostium of the left main coronary artery, i.e., the distal portion of the catheter "prolapses" and loses its preferred orientation within the ascending aorta and left main coronary artery. After this occurs, further advancement of the balloon (or other) working catheter becomes nearly impossible because the Judkins guiding catheter no longer provides adequate support to the highly flexible shaft of the balloon catheter as one attempts to push the balloon catheter across the tight stenosis.

Various attempts to solve this problem are described in the prior art. One of these attempted solutions is set forth in Danforth U.S. Pat. No. 4,909,787 which describes a modified Judkins-type guiding catheter in which the "secondary curve" of the catheter includes a controllable stiffening means. This stiffening means is activated when the Danforth catheter is disposed within the cardiovascular system so that when one attempts to push a balloon catheter across a tight stenosis, the stiffening means on the outer curvature of the secondary curve counters the force exerted against the guide catheter because of the resistance of the stenosis. This stiffening means is said to maintain enough rigidity in the guiding catheter to maintain the tip portion of the guiding catheter within the ostium of the left main coronary artery thereby preventing prolapse of the guiding catheter. Similarly, Danforth U.S. Pat. No. 4,822,345 provides an inflatable/deflatable balloon 50 which works in a manner similar to the catheter in the Danforth U.S. Pat. No. 4,909,787 to increase the rigidity of the distal end of the guiding catheter. Both of these references describe modified Judkins-type guide catheters in which it was attempted to increase balloon catheter backup support by increasing the stiffness of the outer curvature of the distal end portion of the guide catheter and thus prevent the guide catheter from prolapsing during balloon catheter advancement distally across a stenosis. Neither of the Danforth patents attempted to make a fundamental change in the overall shape/configuration of the Judkins-type guide catheter to solve the problem of inferior backup support.

Shiu U.S. Pat. No. 5,098,412 describes a Judkins-type guide catheter having a secondary lumen in addition to a main lumen through which a balloon catheter passes. The secondary lumen structure is separable from the main lumen at the distal portion so that when a distal end of the main lumen of the guide catheter is intubated in the ostium (LMCA), the secondary lumen is moved away from the main lumen (at the distal portion) and may be braced against the opposed walls of a vessel to retain the position of the guide catheter. As in the other attempted solutions to the problem of balloon catheter back up support, the Shiu approach adds bulky complex structure to a Judkins guide catheter instead of fundamentally altering the basic configuration of the Judkins guide catheter to solve the problem. Despite the modification of the Judkins guide catheter, the Shiu guide catheter retains the overall configuration of the Judkins catheter that results in the apex of the secondary curve portion of the Judkins-style guide catheter "banking" of the wall of the ascending aorta at a location substantially above the ostium.

Other solutions include trying to "lock" the tip portion of the Judkins-type guiding catheter within the ostium of the left main coronary artery. For example, Patel U.S. Pat. No. 5,000,743 discloses an inflatable balloon on the distal end of the guide catheter for securing the distal end within the lumen of a coronary artery. Alternatively, Patel U.S. Pat. No. 4,781,682 discloses another type of Judkins-type guide catheter with a "locking" device consisting of support flaps, which expand from the outer surface of the guide catheter, to anchor the distal end portion of the guide catheter adjacent the left main coronary artery. However, these attempted solutions have their own undesirable results. The former solution impedes blood flow through the left main coronary artery and the latter solution introduces additional bulky structure into the cardiovascular system which may hamper the blood flow and interfere with the functioning of the aortic valve. Similarly, Duess U.S. Pat. No. 5,122,125 describes a Judkins-type guide catheter having a "centering" or "locking" top portion in which ridges on the outer surface of the distal tip portion effectively wedge against the inner walls of an ostium to center the tip portion within the ostium. This feature is said to allow proper blood flow around the distal tip portion as well as effectively "anchor" the distal tip portion within the ostium thereby insuring stable and precise positioning of the guide catheter.

These previous modifications of the Judkins catheter for angioplasty have not addressed the primary reason for frequent prolapse of the Judkins-type guide catheter when advancing a balloon catheter across a stenosis: the overall shape of the Judkins guide catheter (prior to insertion in the cardiovascular system) is poorly designed for angioplasty purposes. There are several features of the basic shape of the Judkins guide catheter (for left main coronary arteries or "LMCA") that cause poor performance in using Judkins or slightly modified Judkins guide catheters in angioplasty procedures.

The main deficiency in the previous attempted modifications of the Judkins catheter (as used for guide catheter purposes in the LMCA) has been a lack of appreciation for the extent to which the shape of the Judkins guide catheter prior to insertion in the cardiovascular system affects its performance (i.e., coaxial positioning, backup support) when the Judkins guide catheter is disposed within the cardiovascular system.

The first deficiency in the shape of the Judkins catheter is that the primary curve of the Judkins guiding catheter forms a 90° right angle prior to insertion in the cardiovascular system and is relatively inflexible (the primary curve corresponds to the first curve in the catheter proximal of its utmost distal end). This causes the distal tip portion of the Judkins-type catheter to be incapable of aligning coaxially within the ostium of the left main coronary artery. The 90° angle of the primary curve hampers the ability of the balloon catheter to exit the tip portion of the guiding catheter because this frequently causes the balloon catheter to exit the tip portion into the wall of the left main coronary artery. Accordingly, deep intubation of the distal tip portion within the ostium, which is desirable to increase support for advancing a balloon catheter across a stenosis, is extremely difficult and not practical with the Judkins guide catheter. Moreover, this 90° primary curve also generally limits the distance which the distal tip portion may be intubated into the left main coronary artery.

Similarly, this misalignment of the tip portion prevents the full transfer of pushing force from the proximal end of the balloon catheter to the distal end of the balloon catheter because the balloon catheter must bend around the steeply angled primary curve tip portion of the Judkins-type catheter before aligning properly within the ostium and lumen of the left main coronary artery. This problem with the Judkins guide catheter when used for angioplasty is directly attributable to the belief that one must prevent intubation of the Judkins guide catheter within the ostium and the LMCA. This belief was based on the strong reluctance to put such a catheter into the left main coronary artery because of the relatively large size of diagnostic catheters at time of development of the Judkins catheter.

Moreover, the 90° angle primary curve causes particular problems when attempting to maneuver a balloon catheter into the circumflex branch of the left main coronary artery. The circumflex branch extends from the ostium in the left main coronary artery in a direction almost directly opposite the exit of the balloon catheter from the distal tip portion of the 90° primary curve of the Judkins guide catheter. Accordingly, when attempting to maneuver a balloon catheter into the circumflex branch, the balloon catheter must first negotiate the 90° primary curve of the Judkins catheter and then completely reverse direction (about 180°) to enter the circumflex branch of the left main coronary artery. This significantly attenuates pushing forces transmitted from the proximal end of the balloon catheter to the balloon portion 10 thereby making the crossing of a lesion or stenosis much more difficult.

However, the sharp 90° angle of the primary curve is not the only feature of the shape of the Judkins guide catheter that hampers coaxial placement and stable positioning of the distal tip portion within the ostium of the left main coronary artery. The other main feature of the Judkins guide catheter (for LMCA) is a long straight segment extending distally of the secondary curve (and proximal of the primary curve) and the absence of any other significant curves formed along the length of the catheter (other than the conventional 180° secondary and conventional primary curve). This creates several consequences which combine to cause non-coaxial ostial positioning and poor backup support of the Judkins guide catheter for LMCA.

The first consequence of having the long straight segment extending distally of 180° secondary curve is that when the distal tip and primary curve portion of the Judkins guide catheter are positioned within the ostium of the LMCA, the long straight segment of the Judkins guide catheter distal of the secondary curve (and proximal to the primary curve) extends upwardly from the ostium and across the ascending aorta at a substantial (i.e., sharp) angle so that the Judkins guide catheter contacts the wall of the ascending aorta substantially above the ostium of the LMCA. After contacting the wall of the ascending aorta, the Judkins guide catheter extends proximally away from the aortic wall at a substantial angle (relative the aortic wall) toward the arch of the aorta before again contacting a wall of the descending aorta adjacent the arch of the aorta. Thus, the Judkins guide catheter effectively banks off the wall of the ascending aorta.

The long straight segment extending distally of the 180° secondary curve portion is significant because it is that segment which allows the distal end portion of the Judkins catheter to become anchored within the aortic root complex. This long straight segment (distal of the secondary curve portion) is noticeably longer than the diameter of the ascending aorta and has the following effect: when the utmost distal tip and primary curve portion of the Judkins catheter are intubated within the ostium of the left main coronary, the long straight segment (distal of the secondary curve portion) becomes "wedged", i.e., anchored between the ostium (of LMCA) and the wall of the ascending aorta (where the apex of the secondary curve portion contacts the wall). Without this long straight segment distal of the secondary curve portion, the Judkins guide catheter would slip against the wall of the ascending aorta as one attempted to further advance the guide catheter into the ostium, thereby causing unstable positioning of the Judkins guide catheter.

Accordingly, the long straight segment distal of the secondary curve portion of the Judkins guide catheter is made appreciably longer than the diameter of the ascending aorta so that this "wedging" phenomena occurs. It is because this long distal straight segment is appreciably longer than the diameter of the ascending aorta that the apex of the secondary curve portion contacts the ascending aortic wall substantially above the ostium of the left main coronary artery.

The portion of the Judkins guide catheter that contacts or "banks off" the ascending aortic wall (the contact portion) corresponds roughly to the apex of the curvature of the 180° bend secondary curve. This contact portion is relatively small and approximates a single point on a line such that the contact portion will act as a localized pressure point on the wall of the ascending aorta. It is generally desirable to spread out any pressure exerted on a wall of a blood vessel such as the ascending aorta.

More importantly, the small size of the contact portion in its location substantially above (not directly across from) the ostium of the LMCA directly cause the poor backup support of the Judkins guide catheter when advancing a balloon catheter across a stenosis. First, because the surface area of contact between the contact portion and the aortic wall is so small, the Judkins guide catheter is much easier to dislodge from its position against the wall when resistive "pushback" forces are encountered during advancement of a balloon catheter across a stenosis. Moreover, the straight portion of the Judkins guide catheter (distal of the secondary bend) extends downward through the ascending aorta substantially lateral relative to the contact portion. This allows the stenotic "pushback" forces to more easily overcome the friction of the small contact area between the Judkins guide catheter and the aortic wall and dislodge the Judkins guide catheter from the desired orientation in the aortic complex. However, the potential for dislodging the Judkins catheter from its desired position is not the most disadvantageous aspect resulting from the overall configuration of the 180° secondary curve, 90° primary curve and absence of other curved portions in the Judkins guide catheter.

As explained earlier, the most significant problem associated with the basic shape of the Judkins guide catheter is prolapse (i.e., retracting or "backing out" of the distal tip) of the Judkins catheter from the ostium when advancing the balloon catheter. Prolapse of the Judkins guide catheter occurs because the "pushback forces" are directed along an axis generally parallel to the ostium of the left main coronary artery through the ascending aorta whereas the Judkins guide catheter point of support is a small contact point substantially above the ostium. The stenotic "pushback" forces tend to push the distal tip portion of the Judkins catheter out of the ostium and toward the opposite wall of the ascending aorta. During this prolapse of the distal tip portion, the apex of the secondary curve of the Judkins catheter rests against the aortic wall and acts as a hinge allowing the straight portion (distal of the secondary curve) to bend backwards toward the opposite wall.

The prolapse of the Judkins guide catheter when advancing a balloon catheter is a direct consequence of having a small point of contact against the aortic wall substantially above the ostium. The Judkins guide catheter lacks support to counter pushback forces where it needs it most; directly across from the ostium. The basic positioning of the Judkins guide catheter within the cardiovascular system and ascending aorta is dictated by the basic shape of the catheter when in a relaxed state prior to insertion. In particular, the long straight segment extending distally from the 180° secondary curve (and lack of other curves throughout the length of the catheter other than the primary curve) result in this positioning within the ascending aorta substantially above the ostium of the left main coronary artery. Moreover, recall that attempted solutions (in the Danforth patents) to rectify the prolapse problem of the Judkins guide catheter did not recognize that the basic shape of the Judkins guide catheter was the cause of the prolapse but rather merely added structure to the same basic shape in an attempt to prevent prolapse. Likewise, the Patel patents did not recognize that the problem of prolapse is caused by the basic shape of the Judkins catheter but rather tried to anchor the distal tip portion of the catheter near the aortic root to "lock" the guide catheter within the aortic complex near the ostium. None of the attempted solutions recognize, much less solve, the problem with the Judkins guide catheter—its basic shape prior to insertion in the cardiovascular system—a combination of a primary curve with a 90° angle, a 180° secondary curve with a long straight segment extending distally therefrom, and no other curves throughout the length of the catheter. This configuration results in the absence of a point or axis of support directly across from or opposite the ostium of the left main coronary artery.

Another problem with the Judkins guide catheter is that each bend in the Judkins guide catheter (when disposed fully in the aorta complex) forms at least a 90° angle and or an acute angle (less than 90°). Acute (or 90°) angles in the Judkins catheter cause great resistance to pushing the balloon catheter through the Judkins guide catheter. This happens because the Judkins catheter prior to insertion has only two large curves including the 180° (or 150°) secondary curve and the 90° primary curve, and has no other curved portions throughout its length.

This is significant because the catheter must trace a 180° path around the arch of the aorta and then another 90° turn into the ostium of the left main coronary artery creating an overall path from the descending aorta to the ostium of the LMCA of about 270°. Having fewer curves in the catheter prior to insertion in the cardiovascular system means that as the guide catheter traces this 270° path each curve will form a greater (i.e., sharper) angle and thus, each acute angle will proportionately reduce the transmission of pushing forces when distally advancing a balloon catheter. Conversely, having more curves throughout the length of the catheter in a relaxed state prior to insertion in the cardiovascular system will mean that each curve can form a more moderate (obtuse) angle when the guide catheter is disposed in the cardiovascular system and in particular, the aortic arch and ascending aorta. This allows for an overall better transmission of pushing forces because no single curve will form less than a 90° angle.

The problem of 90° or acute angled (90° or less) bends in the Judkins catheter when fully disposed in the aortic complex illustrates the poor design of the Judkins guide catheter for supporting distal advancement of a balloon catheter through the Judkins guide catheter. Had the Judkins catheter been designed for angioplasty, the configuration of the Judkins guide catheter would incorporate a combination of curved portions so that when disposed in the aorta, the angles of the bends would be milder, i.e., obtuse, to facilitate a fuller transmission of distal pushing forces in the balloon catheter.

Thus, several main problems are attributable to the basic shape of the Judkins guide catheter. First, coaxial intubation is difficult with a 90° primary curve. Second, the point of support of the Judkins guide catheter against the aortic wall acts as a hinge to allow prolapse of the distal tip out of the ostium because the point of support is substantially above the ostium. Moreover, the small surface area of contact between the contact portion and the aortic wall makes it easy to displace the catheter when stenotic pushback forces are encountered. Third, acute angles of the Judkins catheter (when disposed within the aortic complex) reduce the transmission of pushing forces from the proximal end of the balloon catheter to its distal end when attempting to advance the balloon catheter across the tight stenosis.

SUMMARY OF THE INVENTION

The present invention relates to a guiding catheter which is specifically designed to facilitate the maneuvering of a balloon dilatation catheter or other type catheter into a left main coronary artery. Previous catheters used for this purpose include the Judkins-type catheter.

The present invention recognizes that the problem of backup support must be solved by making a fundamental change in the overall shape/configuration of guiding catheters used for left main coronary arteries. This results in a simple guide catheter that is practical in use without the need for complex or bulky adaptations (additional stiffening means, locking devices, or bracing means) to augment the basic guide catheter. In particular, instead of attempting to increase the stiffness of the distal end portion of the Judkins guide catheter or providing a "locking" or "bracing" mechanism to prevent prolapse of the guide catheter, the present invention makes a significant change in the overall shape/configuration of a guide catheter in several ways.

The uniqueness of the guide catheter of the present invention results from having analyzed the factors that determine optimal support of a guide catheter within an aortic root complex and arranging these factors in a way to maximize backup support for distal advancement of a balloon catheter through the guide catheter of the present invention. The factors determining the support provided by the guide catheter include the following. First, coaxial intubation of a distal tip of the guide catheter within the ostium of the left main coronary artery. Second, the lack of steep bends or acute angles throughout the length of the guide catheter when deployed in the cardiovascular system. Third, a point of support of the guide catheter against the wall of the ascending aorta that is directly across from the ostium of the left main coronary artery. Fourth, a large supportive segment of the guide catheter that rests against the wall of the ascending aorta to increase stability of the guide catheter within the aortic complex. Fifth, providing a substantially rectilinear axis of support between the ostium of the left main coronary artery and the point of support against the wall of the ascending aorta. Sixth, providing a straight portion which extends proximally from and at a substantial angle relative to the proximal end of the supportive segment that contacts the aortic wall. Providing a configuration of a guide catheter, such as the present invention, which focuses on combining all of these factors to provide an optimal guide catheter results in a guide catheter that functions appreciatively better than the Judkins guide catheter or previous catheters used for angioplasty catheterization of the left main coronary artery. Although several previous catheters have been discussed, none of these are manufactured or provided on a large scale (other than the Judkins guide catheter) and are not used commonly because they are not practical in use and/or do not sufficiently improve the performance of the basic shape of the Judkins guide catheter from which they are adapted.

An angioplasty guide catheter of the present invention is adapted for use with a left main coronary artery within a cardiovascular system. The guide catheter has a distal end portion such that with a distal tip of the distal end portion coaxially intubated within an ostium of the left main coronary artery (i.e., fully disposed within the cardiovascular system), a portion of the distal end portion contacts and rests against and is substantially contiguous with a wall of the ascending aorta and a distal end of the contact portion is substantially directly opposite the ostium of the left main coronary artery. In addition, a portion of the distal end portion of the guide catheter defines a generally rectilinear axis of support extending from the distal end of the contact portion across the ascending aorta to the ostium of the left main coronary artery.

The guide catheter of the present invention in a relaxed state prior to insertion within the cardiovascular has a configuration that causes the advantageous orientation of the guide catheter in the aortic complex. The guide catheter in its relaxed state includes a first straight portion and a distal end portion. The distal end portion includes a second straight portion extending distally from the first straight portion. A first (or tertiary) curve portion of the catheter is defined by the junction of the first straight portion and the second straight portion and forms a mild obtuse angle of between 130° to 150°. A second (or secondary) curve portion extends distally from the second straight portion and has an overall curvature with an arc of about 150° to 180° and includes at least one curvaceous segments. A third straight portion of the guide catheter extends distally from the secondary curve portion. The arc of the second curve portion is oriented to generally face the interior of the first curve portion. Accordingly, when the second curve portion has an 180° arc, the second straight segment is substantially parallel to the third straight segment. A fourth straight portion of the guide catheter extends distally from the third straight portion to define a primary curve portion of the catheter having an obtuse angle of between 140° to 160°.

The guide catheters of the present invention, yield many advantages over previous prior art guide catheters (such as the Judkins-style guiding catheter). These guide catheters of the present invention have an overall configuration or basic shape that is substantially different than a Judkins-style guide catheter. Accordingly, when the guide catheters of the present invention are deployed in the cardiovascular system, an orientation is achieved within the ascending aorta and ostium of the left main coronary artery that is superior (i.e., better) to the corresponding orientation achieved by a Judkins-style guide catheter.

The primary feature of superior (i.e., better) orientation of the guide catheters of the present invention is that, when disposed in the aortic complex, a contact portion of the guide catheter is established in a substantially contiguous manner against the aortic wall for a substantial length (at least about 1.5 centimeters). Moreover, a distal end of this contact portion is positioned against the aortic wall substantially directly opposite the ostium of the left main coronary artery. This provides a point of support for the guide catheter that directly opposes stenotic pushback forces directed outwardly from the ostium of the left main coronary artery. In addition, a distal tip portion of the guide catheters of the present invention (including the third and fourth straight portions) when disposed in the aortic complex provide a generally rectilinear axis of support that extends substantially across the ascending aorta from the distal end of the contact portion to the ostium of the left main coronary artery. This axis of support substantially directly opposes the axis of the stenotic push back forces thereby substantially diminishing the potential for prolapse of the distal tip portion of the guide catheters of the present invention.

This advantageous orientation of the guide catheters of the present invention (when in the aortic complex) result directly from the configuration of the guide catheters when in a relaxed state prior to insertion in the cardiovascular system. Foremost, the guide catheters of the present invention have a transition portion including the tertiary curve portion and the second straight portion positioned between the first straight portion and the secondary curve portion. The transition portion forms an obtuse angle of between 130° to 150°. This transition portion causes the second straight portion and a proximal portion of the secondary curve portion to form the contact portion (in use) that rests substantially contiguous against the wall of the ascending aorta. The presence of the transition portion causes the second straight portion to rest naturally against the ascending aortic wall thereby allowing the primary point of backup support (at a distal end of the area of support, i.e., a distal end of the contact portion) to be positioned very low in the ascending aorta as compared to the single point of backup support for a Judkins-style catheter. The primary point of backup support for the guide catheters of the present invention is a point along the ascending aortic wall substantially directly opposite the ostium of the left main coronary artery. Moreover, because the second straight portion of the guide catheter of the present invention rests naturally against the ascending aortic wall, a large area of general backup support (the substantially contiguous contact portion) is provided for the guide catheter which makes it quite difficult to dislodge the guide catheter from its desired orientation.

In addition, the presence of the tertiary curve portion provides more bends in the guide catheter (than a Judkins-style guide catheter) when disposed in the aortic complex thereby making each bend in the catheter a milder angle to allow a fuller transmission of distal pushing forces through the guide catheter. Moreover, the mild obtuse angle (about 160°) of the primary curve portion of the guide catheter and the long fourth straight portion (at least about equal to or longer than the third straight portion) cause the distal tip portion to align substantially coaxially within the ostium of the left main coronary artery. The length of the fourth straight portion causes the primary curve portion to be positioned within the ascending aorta, i.e., outside the ostium of the left main coronary artery.

All of these advantages of the guide catheter of the present invention are gained by redesigning the basic configuration of the guide catheter (in its relaxed state). Accordingly, when the guide catheter of the present invention is fully disposed in the aortic complex, a substantially different and superior (i.e., better) orientation is achieved over the previous prior art catheters (e.g. Judkins-style). Moreover, these advantages are achieved without adding additional structure ("locking" mechanism support flaps, "bracing" means, and the like) to the distal end portion of the guide catheter. For example, the guide catheter of the present invention has means for stabilizing (supporting) the guide catheter against (or relative to) the wall of the ascending aorta such that the guide catheter is supported by the ascending aortic wall at a point substantially directly opposite the ostium of the left main coronary artery. Moreover, the means for stabilizing is the contact portion of the guide catheter defined by the second straight portion and the proximal portion of the secondary curve portion. Accordingly, unlike the prior art (e.g. Shiu), the stabilizing means of the guide catheter of the present invention is defined or formed by an outer portion (or surface) of the wall of the tubular member that comprises the guide catheter. The guide catheter of the present invention lacks the complex and bulky structure of the previous prior art catheters that attempted to modify the Judkins-style catheter. Instead, the guide catheter of the present invention provides superior performance by making a fundamental change in the overall shape of guide catheters for the left main coronary artery.

BRIEF DESCRIPTION OF THE DRAWINGS

FIGS. 1A and 1B are side and front views, respectively, of a portion of the catheter of the prior art;

FIG. 1C is a cross sectional view of a portion of a cardiovascular system with the catheter of FIGS. 1A and 1B inserted therein;

FIG. 1D is an enlarged cross-sectional view taken along the line 1D—1D FIG. 1C;

FIGS. 4A-4D and FIGS. 5A-5D are views similar to 1A-1D, respectively, but depicting additional three embodiments of the catheter of the present invention.

FIG. 7 is a plan view of a guide catheter of the present invention.

FIG. 11 is a plan view of a guiding catheter of the present invention.

FIG. 12 is a plan view of a guiding catheter of the present invention.

FIG. 13 is a plan view of a guiding catheter of the present invention.

DESCRIPTION OF THE PRIOR ART

Figures 2A, 2B:
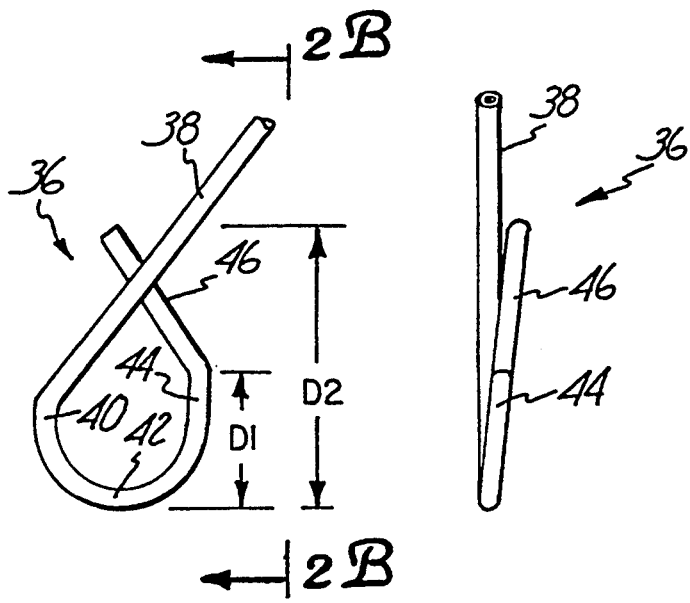
FIGS. 2A-2C, 3A-3C, and 6A-6C are views similar to FIGS. 1A-1C, respectively, but depicting alternate embodiments of the present invention.

Referring to FIGS. 1A and 1B of the drawings, the reference numeral 10 refers, in general, to a well known prior art catheter, commonly referred to as a "Judkins" catheter. The catheter 10 is in the form of an elongated tubular member having a straight portion 12 (shown partially in FIGS. 1A and 1B) and a distal end portion consisting of a straight portion 14 forming an extension of the straight portion 12. The tubular member is bent to form a curved portion 16 which extends from the straight portion 14 for approximately 180°. A straight portion 18 extends from the curved portion 16 and parallel to the straight portion 14. A tip portion 20 extends from, and is perpendicular to, the straight portion 18. A typical Judkins catheter would have straight portions 18 and 20 of 4 centimeters ("cm.") and 1 cm., respectively, in length; and the curved portion 16 would have a radius of curvature of approximately 1 cm. The catheter 10 is usually fabricated of a plastic material selected to exhibit flexibility and softness yet permit adequate "torque control" i.e., the ability to transmit twisting forces along its length so that it can be located and maneuvered precisely within a cardiovascular system by skilled manipulation of its proximal end, as will be described.

A typical cardiovascular system is shown in FIGS. 1C and 1D and is referred to, in general, by the reference numeral 22. The system 22 includes an aorta 24 which extends through the body and curves around for approximately 180° and then branches into a right coronary artery 28 and a left main coronary artery 30. An aortic valve 32 extends between the right coronary artery 28 and the left main coronary artery 30 and is connected to the heart (not shown). As better shown in FIG. 1D, the right coronary artery 28 and the left main coronary artery 30 are normally angularly spaced approximately 120°.

The prior art catheter 10 is designed for use as a diagnostic catheter or a guiding catheter for treatment of stenotic lesions, or the like, in the left coronary artery 30. To this end, the catheter 10 is inserted into the system 22 and is manipulated so that, ideally, the leading, or distal, end portion of the catheter 10 is positioned into the lumen of, the left main coronary artery 30 and used to guide other catheters, such as balloon, laser or atherectomy catheters, or the like (not shown) into the left main coronary artery 30.

To assist in advancing the catheter 10 through the system 22 a relatively stiff wire is initially inserted into the catheter 10 to straighten it out and, after the catheter is completely inserted, the wire is withdrawn, causing the catheter to take the position shown in FIG. 1C. During this procedure, the proximal end portion 10a of the catheter extends outside the system 22 and is manipulated by rotation and guidance in a known manner until the tip portion 20 hopefully aligns with the left main coronary artery 30 in a coaxial relationship. As a result of this operation, the straight portions 14 and 18 are spread apart and the end of the tip portion 20 is inserted in the lumen of the left main coronary artery 30.

However, due to the particular configuration of the Judkins catheter 10, the tip 20 is often misaligned with the left main coronary artery 30 as shown in FIG. 1C, and is thus not located coaxially with the latter artery. Thus, when an inner catheter (not shown) is passed through the catheter 10, the former often strikes the wall of the aorta or left main coronary artery increasing the risk of damage. Also, the catheter 10 does not provide optimum support and guidance of other catheters or devices that are passed through the catheter 10. Further, the curved portion 16, which is shown resting against the inner wall of the aorta 24 in FIG. 1C, is located a considerable distance above the ostium of the artery 30, thus dissipating some of the axial forces transmitted through the catheter during manipulation thereof.

DETAILED DESCRIPTION OF THE PREFERRED EMBODIMENT

The catheter of the present invention is specifically designed to overcome the aforementioned deficiencies of the Judkins type catheter 10, and one embodiment of the catheter of the present invention is shown in general by the reference numeral 36 in FIGS. 2A and 2B. The catheter 36 is in the form of in elongated tubular member having a straight portion 38 (shown partially in FIGS. 2A and 2B) and extending from the proximal end portion (not shown) of the catheter. The catheter 36 includes a distal end portion formed by a straight portion 40, a curved portion 42, another straight portion 44 and a tip portion 46. The straight portion 40 extends at an angle to the straight portion 38, and the curved portion 42 extends from the straight portion 40 for approximately 180°. The straight portion 44 extends from the curved portion 42 and parallel to the straight portion 40, and the tip portion 46 extends from, and at an angle to, the straight portion 44. According to a feature of the embodiment of FIGS. 2A and 2B, the distance D1 (measured vertically as viewed in FIGS. 2A and 2B) between the outer curvature of the curved portion 42 and the junction between the straight portion 44 and 46 is one-half the distance D2 between the latter outer curvature and the end of the tip portion 46.

For example, the distance between the outer curvature of the curved portion 42 and the junction of the straight portion 40 and the straight portion 42 is approximately 1.5 cm., the distance D1 is approximately 2 cm. and the distance D2 is approximately 4 cm. The radius of the curved portion 42 is approximately 1 cm. which forms a diameter of 2 cm. corresponding to the distance between the straight portions 40 and 44. The angle between the straight portions 38 and 40 is between 30° and 50°, and the angle between the straight portions 44 and 46 is between 20° and 50°. It is understood that these distances and angles represent only one possible configuration of the catheter 36. For example, the length of straight portion 40 can be increased to other values within the scope of the invention and thus provide increased support.

The catheter 36 can be fabricated of a material, such as plastic, which exhibits optimum flexibility and softness while permitting the transmission of twisting forces along its length by manipulation of its proximal end.

Figure 2C:
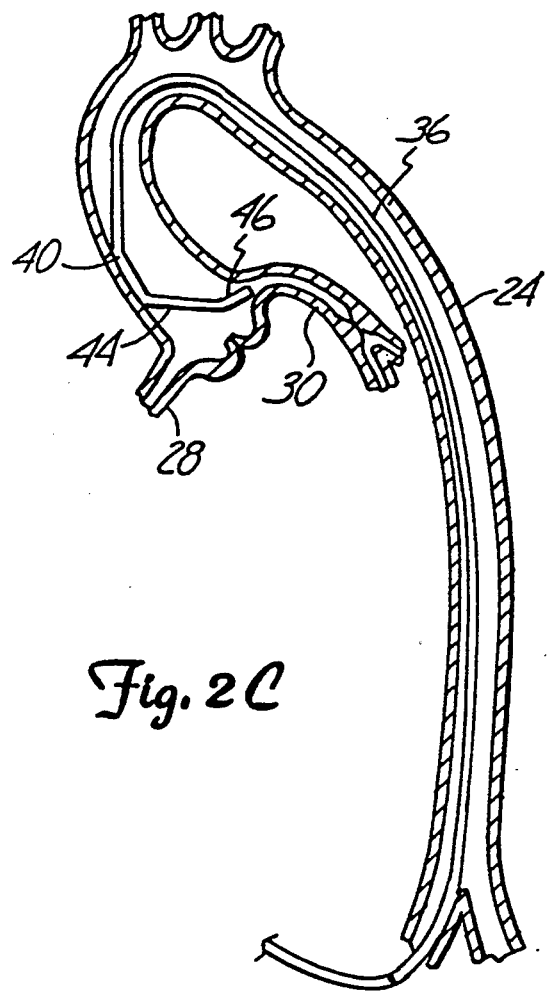

FIG. 2C depicts the cardiovascular system 22 of FIG. 1C with the catheter 36 inserted therein. Prior to insertion a relatively stiff wire (not shown) is inserted in the catheter 36 and the catheter inserted in the system 22. Then the wire is withdrawn and the catheter 36, by virtue of its pre-shape shown in FIGS. 2A and 2B, takes the position shown with the tip portion 46 precisely aligned with the lumen of the left main coronary artery 30 in a coaxial relationship. It is also noted that, as a result of the foregoing, a greater portion of the catheter 36 rests against the inner wall of the aorta 24 and bends at a lesser angle when compared to the Judkins catheter 10. Also the straight portion 40 rests against the inner wall of the aorta 24 and is lower in the artery, and thus more opposite the ostium of the artery 30, when compared to the Judkins catheter 10. Thus, the axial forces transmitted along the length of the catheter 36 are better transmitted to the end portion thereof for more precise manipulation and location.

Figures 3A, 3B:
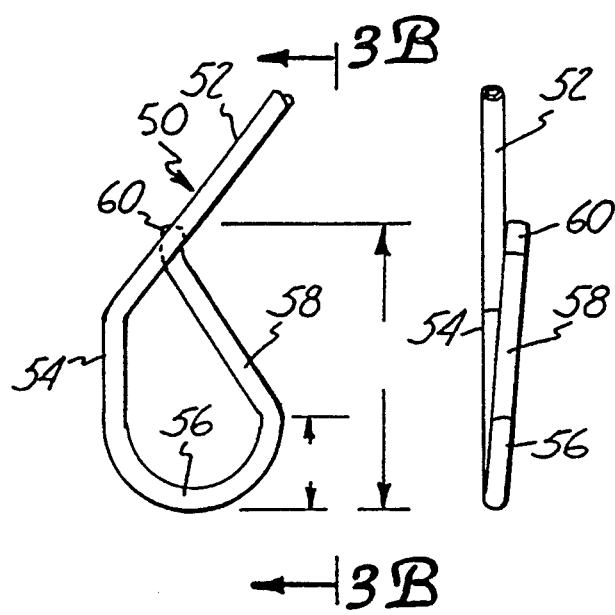

An alternate embodiment of the catheter of the present invention is shown in general by the reference numeral 50 in FIGS. 3A and 3B. The catheter 50 is in the form of an elongated tubular member having a straight portion 52 (shown partially in FIGS. 3A and 3B) and a distal end portion consisting of a straight portion 54, a curved portion 56, a straight portion 58, and a tip portion 60. The straight portion 54 extends at an angle to the straight portion 52, and the curved portion 56 extends from the straight portion 54 for approximately 180°. The straight portion 58 extends from the curved portion 56 at an angle to the straight portion 54. The tip portion 60 extends at an angle to the straight portion 58 and parallel to the straight portion 54. The end of the tip portion 60, which forms the distal end of the catheter 50, extends behind the straight portion 52 as viewed is FIG. 3A.

According to a feature of this embodiment, the distance D1, measured vertically as viewed in FIGS. 3A and 3B, between the outer curvature of the curved portion 56 and the junction between the straight portion 58 and the curved portion 56 is approximately one-third the distance D2 between the latter curvature and the end of the tip portion 60.

For example, the distance between the outer curvature of the curved portion 56 and the junction of the straight portion 52 and the straight portion 54 could be approximately 3.0 cm., the length of the tip portion 60 is approximately 0.5 cm., the distance D1 is approximately 1.3 cm. and the distance D2 is approximately 4.0 cm. The angle that the straight portion 52 makes with the straight portion 54 is between 30° and 50°, and the angle that the straight portion 58 makes with the straight portion 54 is 20°–40°.

Figure 3C:
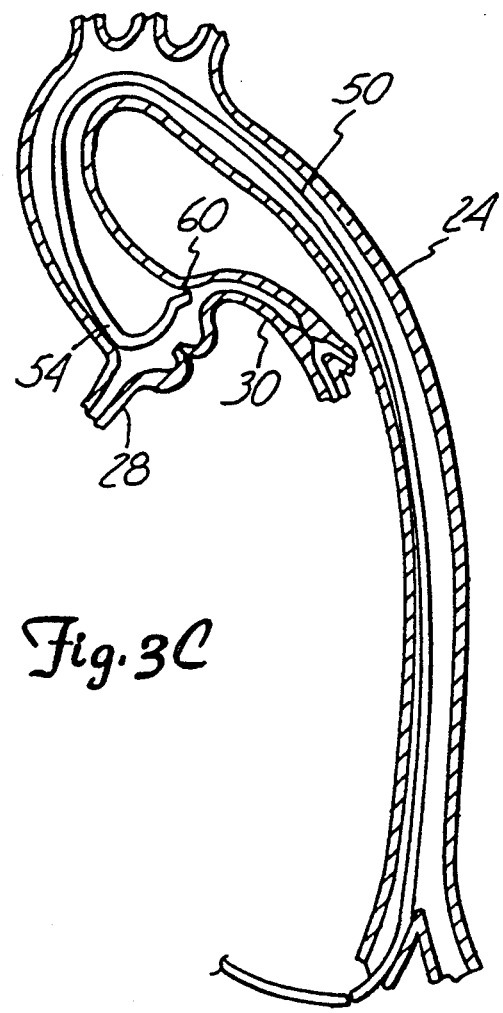

Referring to FIG. 3C, the catheter 50 is inserted in the cardiovascular system 22 in the manner described above. Due to the pre-shape of the catheter 50 shown in FIGS. 3A and 3B, the tip portion 60 is substantially coaxially aligned with the lumen of the left main coronary artery 30 and a portion of the catheter 50 lies in contact with the inner wall of the aorta 24. Thus the embodiment FIGS. 3A–3C enjoys the advantages of the embodiment of FIGS. 2A–2C.

Figure 4A:
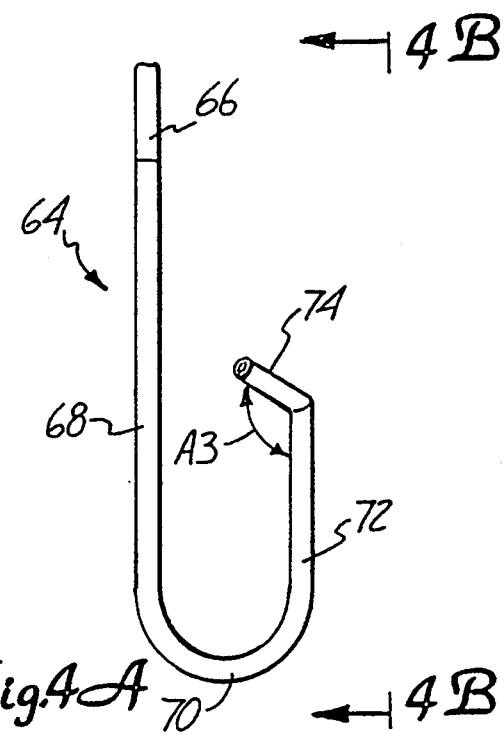
Figure 4B:
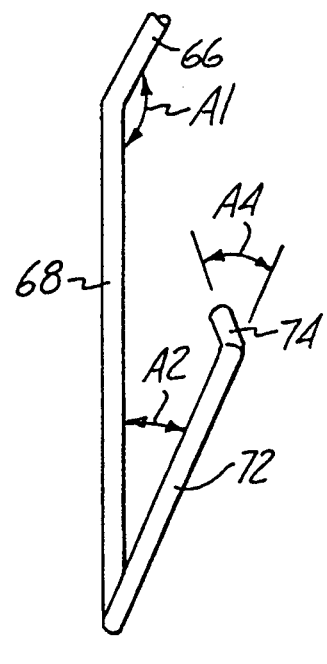

The catheter depicted in the alternate embodiment of FIGS. 4A and 4B is shown in general by the reference numeral 64, and is for a special application commonly referred to as "posterior take-off" of the left main coronary artery, as will be described. The catheter 64 is in the form of an elongated tubular member having a straight portion 66 (shown partially in FIGS. 4A and 4B) extending from the proximal end of the catheter, and a distal end portion consisting of a straight portion 68 a curved portion 70, a straight portion 72 and a tip portion 74. The straight portion 68 extends at an angle to the straight portion 66, and the curved portion 70 extends from the straight portion 68 for approximately 180°. The straight portion 72 extends from the curved portion 70, and the tip portion 74 extends from, and at an angle to the straight portion 72.

As better shown in FIG. 4B, the straight portions 66 and 72 are bent out of the plane formed by the straight portion 68 and the curved portion 70. The straight portion 66 extends at an angle A1 of between 60° and 70°, to the straight portion 68 and the straight portion 72 extends at an angle A2 of between 20° and 40° to the straight portion 68. The length of the portions 68, 72 and 74 are approximately 6 cm., 3 cm. and 1.5 cm., respectively and the radius of the curved portion 70 is approximately 1 cm. The tip portion 74 extends at an angle A3 of between 40° and 50° from the straight portion 72 in a first plane (FIG. 4A), and at an angle A4 from the straight portion 72 (FIG. 4B) of between 25° and 35° in a second plane perpendicular to the first plane.

Figure 4C:
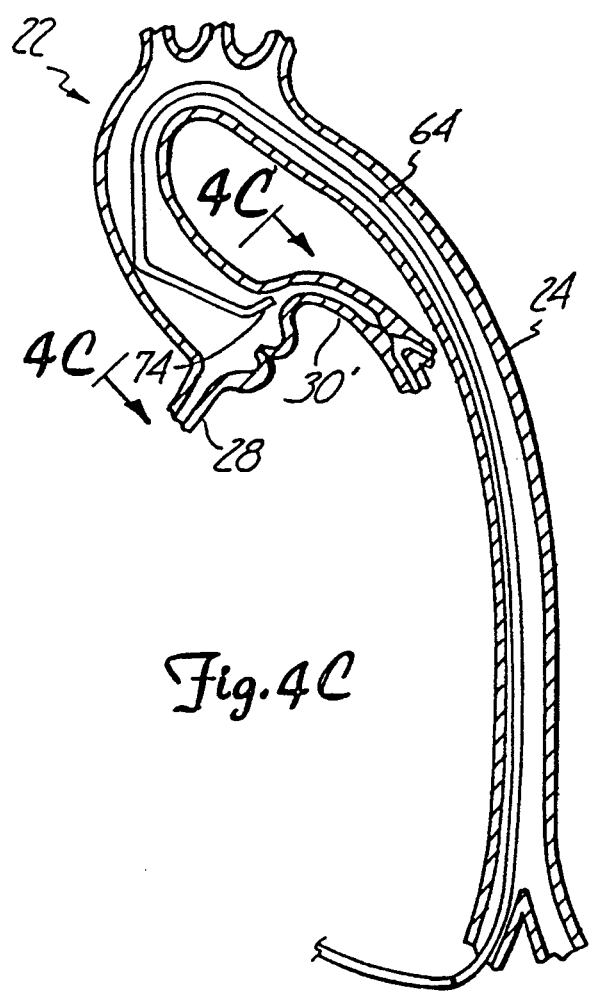
Figure 4D:
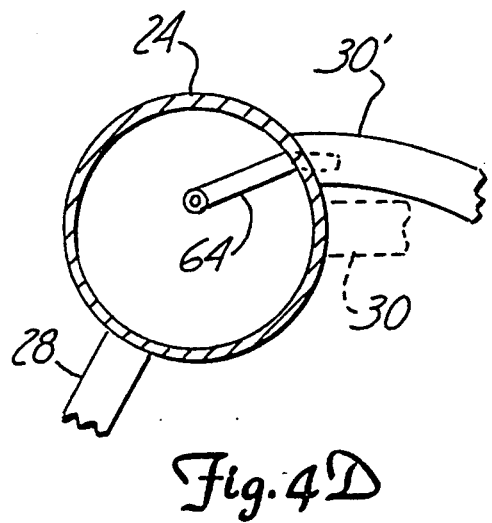

The catheter 64 has a special application in connection with a cardiovascular system 22 in which the left main coronary artery 30 is angularly displaced posteriorly a finite distance from its normal location as shown in FIG. 4D. More particularly, the normal position of the left main coronary artery is shown by the dashed lines and by the reference numeral 30. However the left main coronary artery sometimes is angularly displaced posteriorally from its normal position to a position shown, for example, by the solid lines and by the reference numeral 30. The catheter 64 is especially configured for this location and, when inserted into the cardiovascular system 22 in the manner described above, it takes the position shown in FIG. 4C, with the angled tip 74 coaxially aligned with the lumen of the left main coronary artery 30' notwithstanding the posterior displacement of the artery. The principles of the long tip catheter can also be applied to this catheter 64, particularly adding a 1.5 to 3.0 cm. long segment proximally for better support and extending the tip of the catheter to 2.0 or 2.5 cm.

Another embodiment of the catheter of the present invention is shown in general by the reference numeral 80 in FIGS. 5A and 5B and is also a special application catheter designed for treatment of a right coronary artery that is angularly displaced from its normal position and has an anterior takeoff. More particularly, the catheter 80 consists of a elongated tubular member having a straight portion 82 (shown partially in FIGS. 5A and 5B) and a distal end portion formed by a straight portion 84 and a tip portion 86. The straight portion 84 extends from the straight portion 82 at an angle B1 in a first plane (FIG. 5A) which is between 50° and 70°, and, as shown in FIG. 5B, at an angle B2 in a second plane perpendicular to the first plane which is between 20° and 40°. The tip portion 86 extends from the straight portion 84 and is also angled with respect thereto in two planes. Referring to FIG. 5A, the tip portion 86 extends from the straight portion 84 at an angle B3, which may be between 20° and 30°, in the first plane. As shown in FIG. 5B, the tip portion 86 extends at an angle B4 of between 40° and 50° to the straight portion 84. The length of the straight portions 84 and 86 can be 6 cm. and 1.5–2.0 cm., respectively.

As shown in FIGS. 5C and 5D, the catheter 80 is designed for treatment of a right coronary artery 28' (FIG. 5D) which is shown anteriorly displaced from its normal position shown by the reference numeral 28. As a result of the pre-shape of the catheter 80 shown in FIGS. 5A and 5B, after insertion in the cardiovascular system 22 in the manner described above, it takes the position shown in FIG. 5C with the angled tip portion 86 extending in more coaxial alignment with the lumen of the displaced right main coronary artery 28'.

Figure 6A:
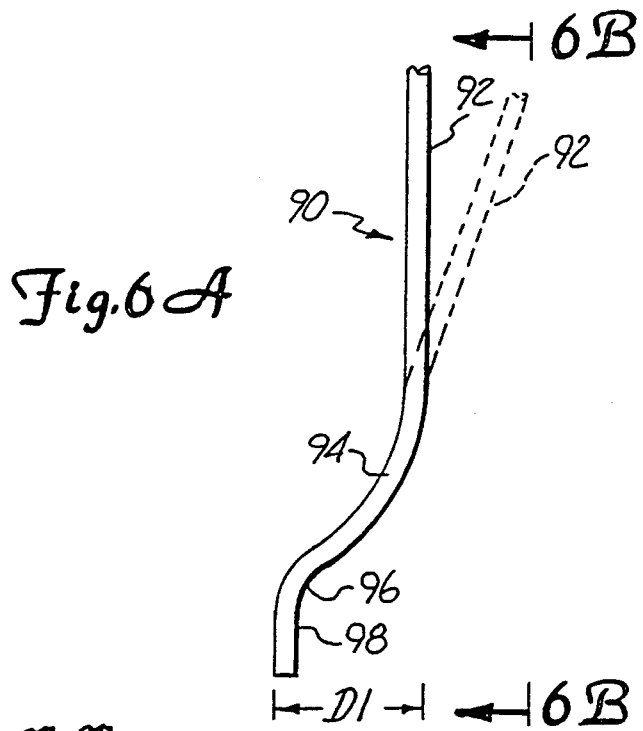
Figure 6B:
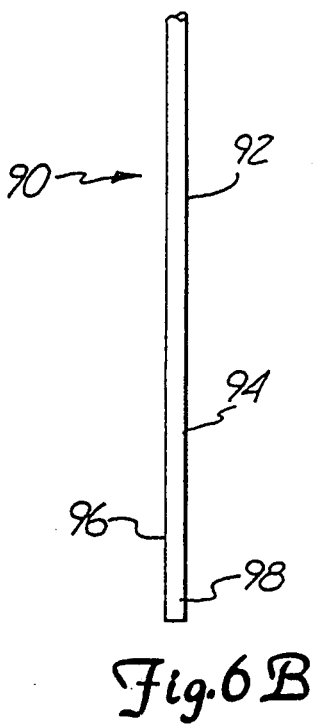

According to the embodiment of FIG. 6A and 6B, a catheter 90 is provided which consists of an elongated tubular member having a straight portion 92 (shown partially in FIG. 6A and 6B) and a distal end portion consisting of a first curved portion 94, a second curved portion 96 and a tip portion 98. The first curved portion 94 is concave (when viewed from the front as shown in FIG. 6B) having a radius of curvature of approximately 3 cm. and its second curved portion is convex having a radius of curvature of approximately 1 cm. The second curved portion 96 continues from the first curved portion 94 when the latter extends approximately 30°–45° from the vertical as shown in FIG. 6A. The length of the tip portion 98 is approximately 1 cm., and the tip portion 98 extends in the same direction as the straight portion 92, i.e. vertically as viewed in FIG. 6A. The lengths of the curves 94 and 96 are such that the outside wall of the tip portion 98 is spaced a distance D1 of approximately 2.5 cm. from the outside wall of the straight portion 92.

Figure 6C:
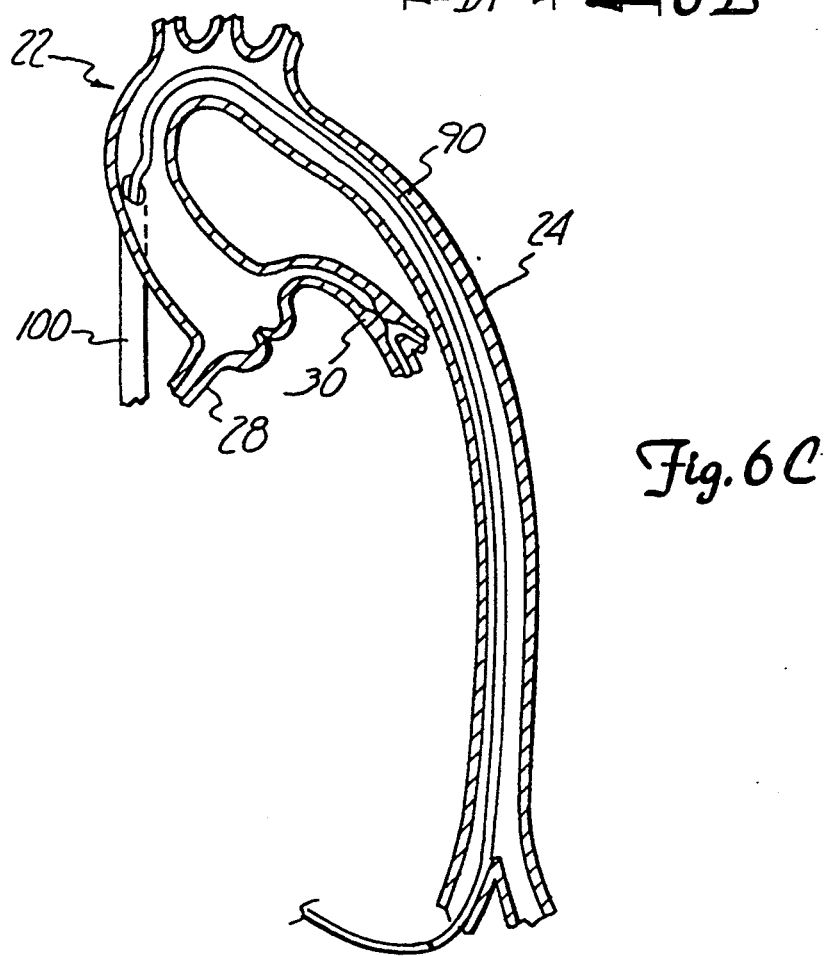

FIG. 6C depicts the cardiovascular system 22 with the catheter 90 inserted therein. The catheter 90 is a special application catheter designed to provide treatment for a venous bypass 100 which connects the aorta 24 to the distal segment of the right coronary artery 28. Due to the pre-shape of the catheter 90 shown in FIGS. 6A and 6B, the catheter, after insertion into the cardiovascular system 22 in the manner described above, it takes the position relative to the lumen of the venous bypass 100 shown in FIG. 6C. In this position the distal end of the tip portion 96, which forms the distal end of the catheter 90 is coaxially aligned with the lumen of the venous bypass 100.

According to an alternate embodiment of the catheter 90, the straight portion 92 can extend to an angle of approximately 10° to 30° to the vertical, as viewed and shown by the dashed line in FIG. 6A.

It is thus seen that the catheters embodied in the present invention are each specifically configured for more precise coaxial alignment with a particular artery in the cardiovascular system. Also, the catheters of the present invention provide improved support and guidance of associated catheters, such as balloon catheters, during angioplasty. Further, the catheters of the present invention form relatively small angles when inserted in the cardiovascular system, thus minimizing the dissipation of axial force during use.

Moreover, additional embodiments of the guide catheters present invention for catheterization of a left main coronary artery provide further illustration of the features of embodiments of the present invention described above for catheterization of a left main coronary artery. These additional embodiments of the present invention include the same strategically ordered sequence of straight portions, curve portions, and transition portions resulting in more precise coaxial alignment of the guide catheter within an artery, increased support and guidance for balloon catheters, and a fuller transmission of pushing forces. The previously described guide catheter embodiments of the present invention for catheterization of a left main coronary artery, e.g., the guide catheter embodiment of FIG. 2A, and these additional embodiments include a unique transition portion created between an otherwise conventional first straight portion and an otherwise conventional secondary curve portion of the guide catheter of the present invention. This transition portion in the previously described embodiment (e.g., the FIG. 2A embodiment) and these additional embodiments include a tertiary curve portion (in FIG. 2A, the curved portion between the first straight portion 38 and the second straight portion 40) and a second straight portion (40 in FIG. 2A). These additional embodiments also include the long fourth straight tip portion (46 in FIG. 2A) and the mild angle primary curve portion of the FIG. 2A embodiment. These additional embodiments provide further examples illustrating the strategic sequencing of straight, curved, and transition portions that yield the many advantages of the guide catheters of the present invention, particularly those used for catheterization of a left main coronary artery.

A guide catheter 110, another preferred embodiment of the present invention, is illustrated in FIG. 7. The guide catheter 110 is adapted for use with a left main coronary artery to facilitate advancement of a dilatation balloon catheter (or other intravascular devices) through the guide catheter 110. The guide catheter 110 is shown in FIG. 7 in a relaxed or "equilibrium" state prior to insertion into the cardiovascular system and includes an elongate flexible tubular shaft 112 which extends from a proximal portion 114 to a distal portion 116. The guide catheter 110 includes a first straight portion 118 and a distal end portion 119 extending distally from a distal end of the first straight portion 118. The first straight portion 118 of the guide catheter 110 extends from a proximal end 120 of the catheter 110 to a point 122 (a distal end of the first straight portion 118) located distally along the shaft 112 (distal of the proximal end 120). The first straight portion 118 preferably has a length of about 90 to 95 centimeters but can be made shorter or longer to accommodate different patient anatomies.

A tertiary curve portion 123 of the guide catheter 110 is defined by the curvature in the catheter 110 between the point 122 and a point 126 (a distal end of the tertiary portion 123) located distally along the catheter shaft 112 relative to the point 122. A second straight portion 124 of the guide catheter 110 extends rectilinearly between the point 126 and a point 128 (a distal end of the second straight portion) located distally along the catheter shaft 112 from the point 126. The curvature of the tertiary curve portion 123 creates an obtuse angle between the first straight portion 118 and the second straight portion 124 of between 130° and 150°. As shown in FIG. 7, the obtuse angle of the tertiary curve portion 123 is about 140° and the curvature of the tertiary curve portion 123 is smooth and uniform. The tertiary curved portion 123 and the second straight portion 124 together define a transition portion 125 of the guide catheter 110 forming an obtuse angle of between 130° to 150° between a distal end of the first straight portion 118 and a proximal portion of a secondary curve portion 130 of the guide catheter 100.

The secondary curve portion 130 of the guide catheter 110 is defined by the curvaceous segment of the catheter shaft 112 extending from the point 128 to a point 132 (a distal end of the curve portion 130) located distally along the shaft 112 (distal of the point 128). The transition portion 125 of the guide catheter 110 is a curvaceous segment (having at least one curved or angled portion) comprised of the preferred combination of two discrete portions: the tertiary curve portion 123 and the second straight portion 124. The transition portion 125 causes the proximal portion 131 of the secondary curve portion 130 (and the second straight portion 124) to form the preselected obtuse angle of between 130° and 150° relative to the first straight portion 118 (both in a relaxed state and as deployed in the cardiovascular system).

The secondary curve portion 130 forms a curvaceous segment (having at least one curve or angled portion) and defines a transition portion having a smooth curvature or being a combination of discrete straight and angled segments forming an overall curvature with an arc of approximately 150° to 180° between the point 128 (the distal end of the second straight portion 124) and the point 132 (the proximal end of the third straight portion 134).

A distal tip portion of the guide catheter 110 includes a third straight portion 134 and a fourth straight portion 138. The third straight portion 134 of the guide catheter 110 extends from the point 132 distally along the catheter shaft 112 to a point 136. A primary curve portion 137 of the guide catheter 110 is defined by the curvature of catheter shaft 112 between point 136 (a distal end of the third straight portion) and a point 140 located distally along the catheter shaft 112 (distal from the point 136). The fourth straight portion 138 of the guide catheter 110 extends distally from the point 140 and together with the third straight portion 134 defines the distal tip portion of the guide catheter 110. The primary curve portion 137 has an obtuse angle of approximately 140° to 160° formed between the third straight portion 134 and the fourth straight portion 138, and as shown in FIG. 7 has an obtuse angle of about 160°.

The arc of the secondary curve portion 130 generally faces the interior of the obtuse angle of the primary curve portion 137. Accordingly, when the arc is 180°, the second straight portion 124 and the third straight portion 134 are substantially parallel to each other.

The second straight portion 124 preferably extends rectilinearly at least about 1.5 centimeters. The third straight portion 134 extends rectilinearly about 0.5 centimeters and the fourth straight portion extends rectilinearly about 1.5 centimeters. The second straight portion 124 can have a length slightly less than 1.5 centimeters if desired. The radius of the secondary curve portion 130 perferably is about 1 centimeter.

Although the guide catheter 110 can be a single piece of tubing with a uniform degree of flexibility throughout its length, the guide catheter 110 preferably is made of two or three principal tubular segments with each successively distal segment having a greater degree of flexibility. As seen in FIG. 7, the embodiment of the guide catheter 110 having three principal flexibility segments includes a first flexibility tubular segment 142 extending from the proximal end 120 of guide catheter 110 to a bond member 148 located at a distal portion of the third straight portion 134 (in the distal portion 116 of the guide catheter 110). A second flexibility tubular segment 144 extends distally from the bond member 148 to a third flexibility tubular tip segment 146. The nature of the three principal segments and their different flexibility are described in co-pending application Ser. No. 07/908,250 INTRAVASCULAR GUIDE CATHETER and which is incorporated by reference herein. In one embodiment, the first segment 142, the second segment 144, and the third segment 146 have a Shore D durometer hardness of about, 63, 40, and 35 respectively. The bond member 148 has a Shore D durometer hardness of about 50, intermediate the hardness of the first segment 142 and the second segment 144.

A double flexibility segment embodiment (not shown) of the guide catheter 100 has two principal segments of flexibility, each with a different degree of flexibility. The double flexibility embodiment has a tip segment (like tip segment 146) with a select degree of flexibility and a main segment (all portions proximal to the tip segment) with a different select degree of flexibility. The double flexibility segment embodiment differs from the triple flexibility segment embodiment in that the second flexibility segment 144, having a hardness intermediate that of the first (i.e., main) flexibility segment 142 and the tip segment 146, is absent in the double flexibility segment embodiment. Although it is preferred to have a bond ring member (like member 148) positioned between the main and tip flexibility segments, the double flexibility segment may omit a bond ring member between the main segment and the tip segment. The main segment of the double flexibility segment embodiment of the guide catheter 110 has a Shore D hardness of 63 (or 67, 70) and the tip segment has a Shore D hardness of 35. The optional bond ring member would have a Shore D hardness (e.g., about 46) intermediate that of the first segment and tip segment.

The catheter shaft 112 of both the double flexibility segment embodiment and the triple flexibility segment embodiment (FIG. 7) are made of an outer layer and an inner layer. The outer layer is preferably formed of a polyether block amide material, such as PEBAX ® available from ATOCHEM, INC. (Glen Rock, N.J.) and a radiopaque compound, such as bismuth carbonate. The inner layer is a coating of lubricous material such as TEFLON ® available from E. I. DuPont Nemours & Co. (Wilmington, Del.). The first principal segment 142 and the second (intermediate) segment 144 (in the triple flexibility embodiment) preferably have a reinforcing layer of wire braiding (of stainless steel wire) extending along the catheter shaft 112 between the inner layer and the outer layer.

Figure 8A:
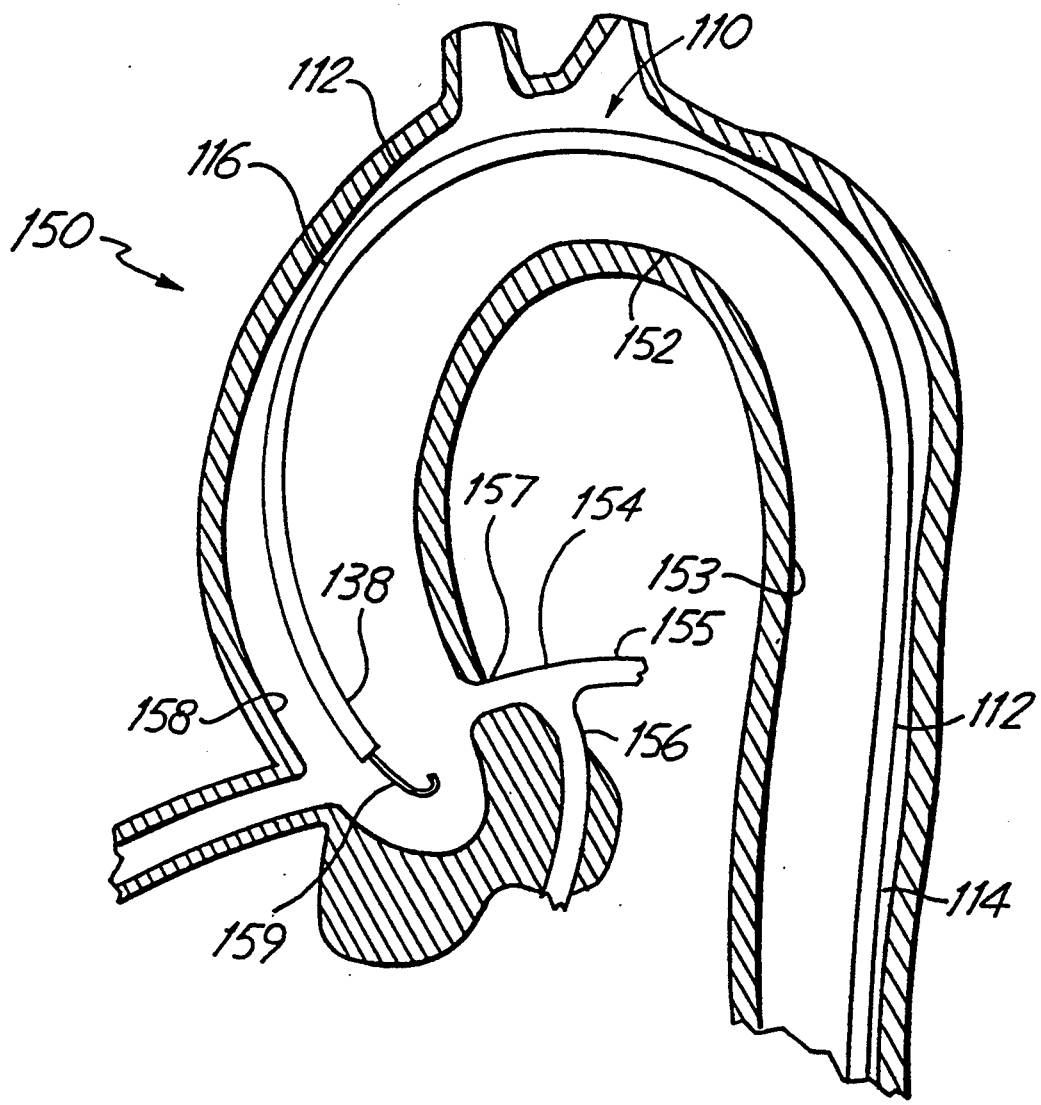
FIG. 8A is a cross-sectional view of a portion of a cardiovascular system with a guiding catheter of the present invention disposed therein along with a positioning wire extending through the catheter.

In use, as shown in FIG. 8A, the guide catheter 110 is inserted through the cardiovascular system so that its distal end portion 119 is disposed within the aortic complex including an ascending aorta 158, an arch of the aorta 152, and a descending aorta 153. A left main coronary artery 154 extends laterally from the ascending aorta 158 and has a left anterior descending (LAD) branch 155 and a circumflex (CFX) branch 156. An ostium 157 of the left main coronary artery 154 forms an interface with the ascending aorta 158.

The guide catheter 110 is inserted into the cardiovascular system at a femoral artery (not shown) with a stiff wire 159 extending through the entire length of the lumen of the guide catheter 110. The stiff wire 159 is of sufficient rigidity to temporarily overcome the curve portions of the guide catheter 110 so that the guide catheter 110 takes on the shape of the stiff wire 159 as the stiff wire 159 passes through the cardiovascular system. The guide catheter 110 (with the stiff wire 159 therein) are advanced distally through the cardiovascular system until the fourth straight portion 138 of the guide catheter 110 is adjacent the ostium 157 of the left main coronary artery 154 (as shown in FIG. 8A).

As seen in FIG. 8A, the guide catheter 110 (with the wire 159 extending therethrough) forms a relatively smooth curve to extend about the arch of the aorta 152 and down through the ascending aorta 158. Once the catheter 110 is in position adjacent the left main coronary artery 154, the stiff wire 159 is removed from within the guide catheter 110 allowing the guide catheter 110 to attempt to resume its relaxed state configuration (the relaxed state shape prior to insertion in the cardiovascular system, as shown in FIG. 7). This results in the guide catheter 110 assuming the orientation as shown in FIG. 8B.

Figure 8B:
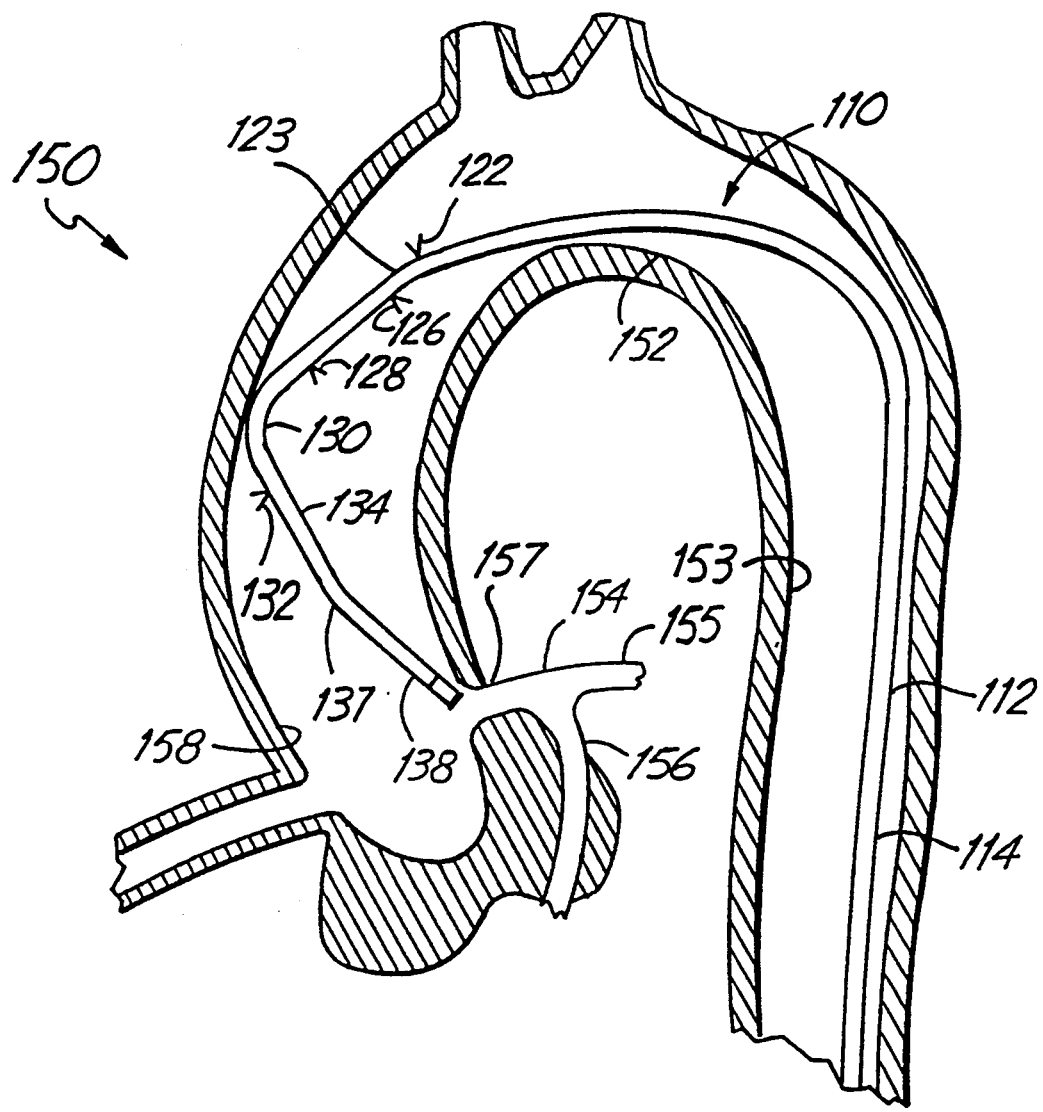
FIG. 8B is a cross-sectional view of the cardiovascular system with a guiding catheter of the present invention disposed therein without the positioning wire extending therethrough.

The orientation and shape of the guide catheter 110 as shown in FIG. 8B illustrates that the curved portions of the catheter 110, primarily the secondary curved portion 130, reassert their original curvatures as much as possible while being limited by the structure of the ascending aorta 158 and the arch of the aorta 152. The secondary curved portion 130, while trying to reassert its original 180° curvature, forces the fourth straight tip portion 138 of guide catheter 110 toward and against (or near) a wall of the ascending aorta 158 adjacent the ostium 157 of the left main coronary artery 154. However, the secondary curve portion 130 is limited from regaining its full 180° curvature because the contact of the fourth straight portion 138 against the wall of the ascending aorta 158 prevents the secondary curved portion 130 from fully returning to its original curvature. This creates stored energy within the secondary curve portion 130 of the guide catheter 110. Similarly, the tertiary curved portion 123 is prevented from returning fully to its original curvature such that energy is also stored within the catheter shaft 112 in the region of the tertiary curved portion 123.

Figure 8C:
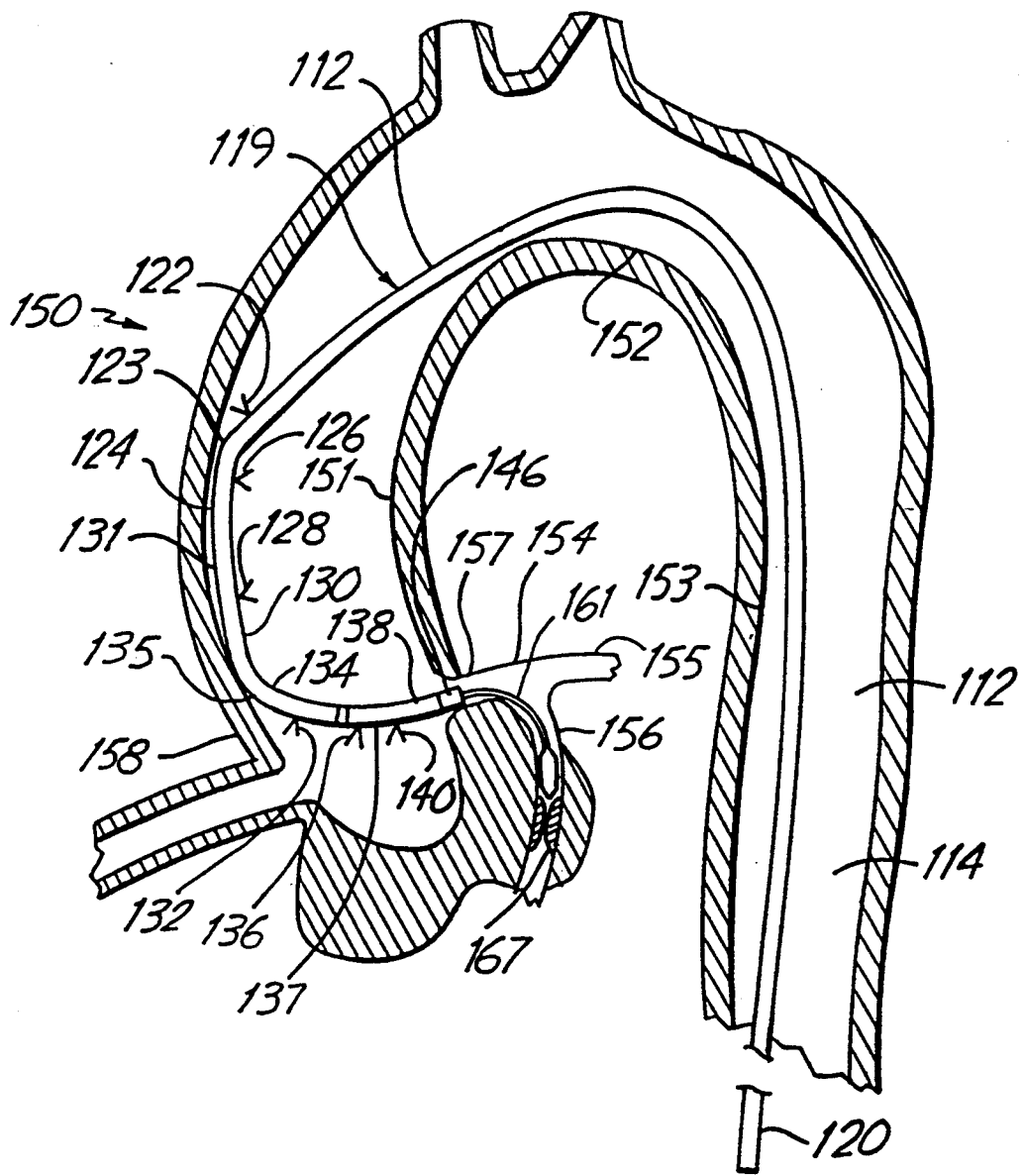
FIG. 8C is a sectional view of the cardiovascular system with a guiding catheter of the present invention fully disposed therein and having a balloon catheter extending therethrough.

The guide catheter 110 is advanced distally further from the orientation shown in FIG. 8B and maneuvered until in the orientation shown in FIG. 8C. This orientation (FIG. 8C) corresponds to the proper positioning of the guide catheter 110 within the cardiovascular system so that the guide catheter 110 can facilitate the advancement and support of a balloon dilatation catheter 161 through the guide catheter 110. As seen in FIG. 8C, the distal end portion 119 of the guide catheter 110 is positioned within the aortic complex such that the tertiary curved portion 123 is disposed against (or very near) a wall of the ascending aorta 158. The second straight portion 124 of the guide catheter 110 extends distally from the tertiary curve portion 123 to rest against and be substantially contiguous with the wall of the ascending aorta 158. As disposed within the ascending aorta 158 as shown in FIG. 8C, the tertiary curved portion 123 generally assumes its relaxed state (preinsertion shape) obtuse angle of about 130° to 150° such that the second straight portion 124 rests naturally against the wall of the ascending aorta 158, i.e., retaining little or no stored energy in the tertiary curved portion 123. This lack of stored energy in the tertiary curve portion 123 promotes stability in the guide catheter 110 to retain its desired orientation in the ascending aorta because the guide catheter 110 will not attempt to release any undesired stored energy.

As seen in FIG. 8C, a proximal portion 131 of the secondary curved portion 130 extends distally from the second straight portion 124 and also rests against and substantially contiguous with the wall of the ascending aorta 158. Accordingly, the second straight portion 124 and the proximal portion 131 of the secondary curved portion 130 together define a contact portion of the guide catheter 110 for resting against and substantially contiguous with the wall of the ascending aorta 158. From its distal end 135, the contact portion extends along the ascending aortic wall generally above the ostium 157, as seen in FIG. 8C. A remaining distal portion of the secondary curved portion 130 (beginning with approximately the apex of its pre-insertion, i.e., relaxed state, curvature) extends laterally away from the wall of the ascending aorta 158 so that the third straight portion 134 and the fourth straight portion 138 together extend laterally across the ascending aorta 158 wherein the distal end of the fourth straight portion 138 coaxially intubates within the ostium 157 of the left main coronary 154.

As seen in FIG. 8C, the third straight portion 134 of the guide catheter 110 extends slightly downward as it extends across the ascending aorta 158 from the distal portion of the secondary curve portion 130 near the wall of the ascending aorta 158.

The primary curved portion 137 of the guide catheter 110 is shown in FIG. 8C, resting in its natural relaxed state orientation of about 160° (e.g. 140° to 160°) which causes the fourth straight portion 138 of the distal end portion of the guide catheter 110 to extend slightly upward through the ascending aorta 158 until the distal end of the fourth straight portion 138 intubates within the ostium 157. The third straight portion 134 and the fourth straight portion 138 (when properly positioned within the aortic complex as shown in FIG. 8C) together define a generally rectilinear axis of support extending across the ascending aorta from a point along the wall of the ascending aorta substantially directly opposite the ostium to the ostium. Although the third and fourth straight portions extend a substantial distance across the ascending aorta, the distal portion of the secondary curve portion 130 spans the remaining distance across the ascending aorta 158.

In this preferred orientation shown in FIG. 8C, a distal end 135 of the contact portion (the contact portion including the second straight portion 124 and a proximal portion 131 of the secondary curved portion 130) rests against the wall of the ascending aorta 158 at a point substantially directly across from the ostium 157 of the left main coronary artery 154. This preferred orientation of the guide catheter 110, with the contact portion resting against and substantially contiguous with the wall of the ascending aorta 158 and the distal end 135 of the contact portion positioned substantially directly across from the ostium 157, can be achieved with virtually any anatomical variation in the ascending aorta 158 and the arch of aorta 152. The orientation of the guide catheter 110 as shown in FIG. 8C has extremely important advantages in supporting advancement of a balloon catheter across the stenosis 167 (as shown in the circumflex branch 156 of the left main coronary artery 154). Moreover, this advantageous orientation of the guide catheter 110 within the aortic complex is directly attributable to the shape and configuration (including a particular sequence of straight and curved portions) of the guide catheter 110 in its relaxed state prior to insertion in the cardiovascular system.

A primary structural advantage of the guide catheter 110 (in its relaxed state) is the presence of a mild obtuse angle transition portion (the tertiary curve portion 123 and the second straight portion 124) located proximal of the secondary curve portion 130 in the guide catheter 110. This transition portion directly causes the second straight portion 124 and the proximal portion of the secondary curve portion 130, when fully disposed in the ascending aorta 158, to form the contact portion that rests substantially contiguous with the wall of the ascending aorta 158. Having a contact portion resting substantially contiguously against a back wall of the ascending aorta 158 causes the distal end 135 of the contact portion to be disposed substantially directly across from the ostium of the left main coronary artery. This provides a primary point of backup support for the guide catheter 110 directly opposite the ostium. Accordingly, when resistive forces are exerted by a tight stenosis and pushed back on the guide catheter 110, the guide catheter 110 has back up support provided by the distal end 35 of the contact portion to effectively counter the stenotic "pushback" forces. This prevents the guide catheter 110 from prolapsing (i.e., being pushed out) out of the ostium 157 because, as seen in FIG. 8D, the primary point of support is directly opposite the direction of the stenotic "push back" forces.

The direct opposition of the pushback forces by the point of backup support is further complemented by the third straight portion 134 and fourth straight portions 138 because those portions together define a generally rectilinearly axis of support extending from the ostium across the ascending aorta to the point of support (the distal end 135 of the contact portion) resting against the wall of the ascending aorta 158. This axis of support direct opposes the stenotic pushback forces and substantially eliminates any possibility of the "pushback" forces leveraging or bending the third and fourth straight portions out of the ostium 157.

Figure 8E:
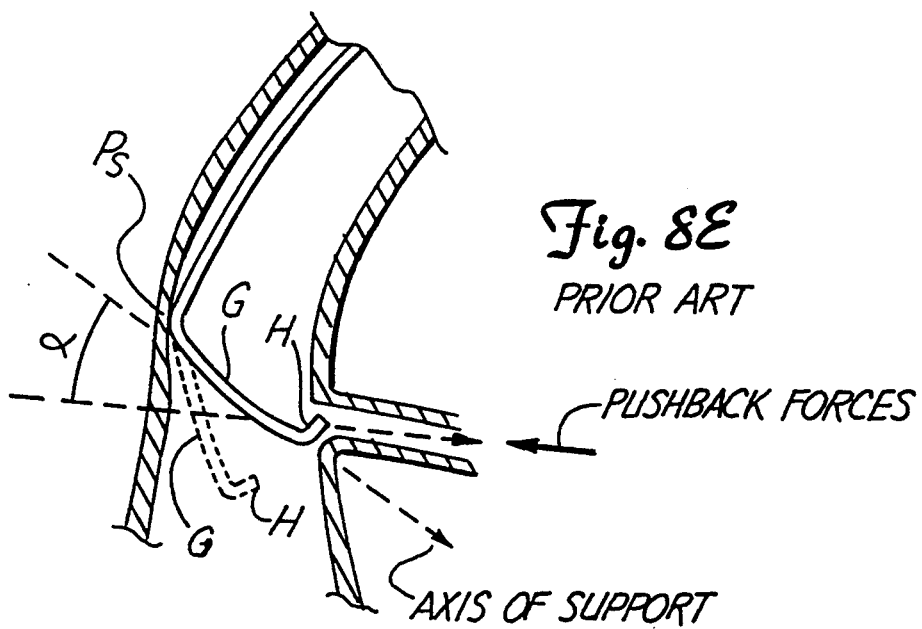
FIG. 8E is a cross-sectional view of a portion of a cardiovascular system with a Judkins guide catheter of the prior art disposed therein.
Figure 8D:
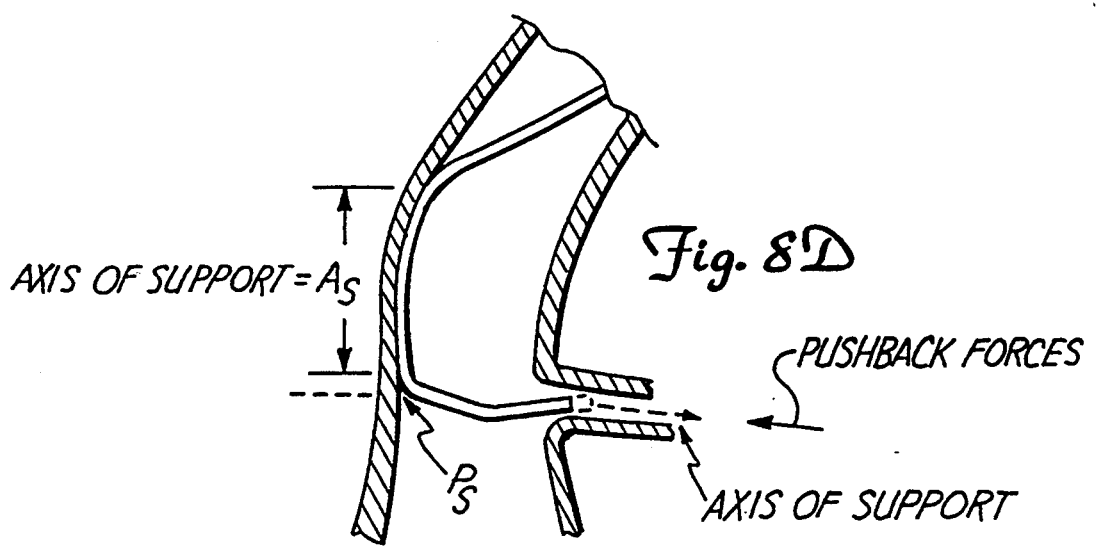
FIG. 8D is a cross-sectional view of a portion of a cardiovascular system with a guiding catheter of the present invention disposed therein.

FIG. 8E illustrates the action of the stenotic "pushback" forces leveraging the distal tip portion of the Judkins prior art guide catheter out of a ostium (see phantom lines showing prolapsed distal tip portion). This prolapsing of the Judkins guide catheters occurs because the point of support $P_s$ (which is provided (approximately) by the apex of the secondary curve portion) rests against the wall of the ascending aorta substantially above the ostium of the left main coronary artery. This results from the long straight segment G of the Judkins guide catheter that extends from the ostium across the ascending aorta to the "back" wall of the ascending aorta at a substantial angle and thus creating an axis of support for the Judkins guide catheter to be at substantial angle $\alpha$ relative to the axis of the "stenotic" pushback forces. Accordingly, when pushback forces exerted against the Judkins guide catheter become sufficiently large, the distal tip portion of the Judkins guide catheter prolapses because the pushback forces are only indirectly opposed by the Judkins guide catheter.

Indeed, the primary backup support for the Judkins guide catheter apparently results not from a structural axis of support and point of support but rather from energy stored in secondary curve portion of the Judkins guide catheter because the secondary curve wants to regain its natural pre-insertion 180° (or 150°) curvature. Accordingly, this stored energy tends to force the straight segment G and segment H of the Judkins guide catheter toward and into the ostium. Once the stenotic pushback forces exceed this stored energy in the secondary curve portion of the Judkins catheter, no substantial structural support is available from the guide catheter to provide support against the pushback forces because the axis of support does not directly (and sufficiently) oppose the axis of pushback forces. Instead, the point of support for the Judkins guide catheter (substantially above the ostium) acts like a hinge as the pushback forces bend the straight segment G (and segment H) away from the ostium into the "prolapse" position shown by the phantom lines.

The guide catheter 110 of the present invention does not rely on stored energy in the secondary curve portion 130 to counter stenotic pushback forces directed proximally through the balloon catheter. Rather, any stored energy in the secondary curve portion 130 tends to maintain the fourth straight portion 138 in a position directed slightly upward into the ostium 157 of the left main coronary artery 154. The stenotic pushback forces are countered by the guide catheter 110 of the present invention by structural support in two ways: from the primary point of backup support substantially directly across from the ostium and from the generally rectilinear axis of support provided by a combination of the third and fourth straight portions extending across the ascending aorta.

Moreover, the guide catheter 110 has a large area of support ($A_s$) between the substantially contiguous contact portion and the wall of the ascending aorta, thereby creating a significant interface of friction therebetween. This effectively anchors the contact portion against the ascending aortic wall. Thus, to extent that any stenotic pushback force acts laterally relative to the axis of support, the guide catheter 110 will be unlikely to become dislodged from its desired orientation in the aorta. Moreover, a greater force can be applied when distally advancing a balloon catheter through the guide catheter 110 because the guide catheter 110 will be less likely to become dislodged (i.e., slip) because of the larger area of support. This substantially contiguous contact portion also reduces the possibility of dissection of the ascending aorta 158 because the stenotic "pushback" forces exerted on the aortic wall are spread out and thus substantially minimized at any particular point along the aortic wall.

The superior backup support of the guide catheter 110 of the present invention is achieved primarily from the point of support (provided by the distal end 135 of the contact portion) being positioned substantially directly across from the ostium of the left main coronary artery. The tertiary curve portion 123 of the transition portion permits the substantially contiguous positioning of the contact portion against the aortic wall and more importantly, the positioning of the distal end 135 of the contact portion "low" within the ascending aorta 158. This result is achieved because the obtuse angle of the tertiary curve portion 123 is substantially the same (about 140°) when the catheter 110 is disposed fully within the aortic complex as the curvature of the tertiary curve portion 123 in its relaxed state prior to insertion within cardiovascular system (about 140°). This reduces the problem of localized (initial contact with the ascending aorta) unnecessary stored energy within the guide catheter 110. This lack of stored energy allows the second straight portion 124 to rest naturally against the wall of the ascending aorta 158 because no force is attempting to direct the second straight portion 124 toward the ostium as occurs with segment G of the Judkins guide catheter (see FIG. 8E). Accordingly, a distal end of the second straight portion 124 (and the proximal portion 131 of the secondary curved portion 130) can rest against the aortic wall very low in the ascending aorta 158. Without this transition portion including tertiary curve portion 123 and the second straight portion 124, the conventional orientation of previous (Judkins-type) guide catheters would result in which a straight portion extends away from the ascending aortic wall because the secondary curve portion "banks" off the aortic wall (like a single point on a line) as shown in FIG. 8E.

In addition to the structural support advantages from the tertiary curve portion 123, the guide catheter 110 of the present invention also has an advantageous long distal tip portion with a primary curve having a mild obtuse angle. The fourth straight portion 138 of guide catheter 110 is longer than the third straight portion 134 of the guide catheter 110 resulting in the primary curve portion 137 being located within the ascending aorta 158 outside of the ostium of the left main coronary artery (unlike the Judkins primary curve which is positioned within the ostium). As shown in FIG. 8C and 8D, the primary curve portion 137 is positioned about halfway between the aortic wall and the ostium. However, the length of the fourth straight portion 138 can be about equal to (or even slightly less) than the length of the third straight portion 134 if necessary so that depending on patient anatomy the primary curve portion 137 is preferably (not necessarily) positioned within the ascending aorta halfway between the back wall of the ascending aorta and the ostium. Similarly, a fourth straight portion in later embodiments (FIGS. 9–13) of the present invention need not be longer than a third straight portion of those guide catheters. Moreover, the obtuse angle between the fourth and third straight portions is quite mild (about 160°) which yields an overall generally rectilinear axis of support extending from the contact portion of the guide catheter 110 against the aortic wall across the aorta and into the ostium 157.

This provides several advantages. First, because the obtuse angle between the fourth straight portion 138 and third straight portions 134 is relatively mild (between about 140° and 160°), this avoids dissipating pushing forces applied to advance the balloon catheter distally through the left main coronary artery 154 and across a tight stenosis. Second, this unique configuration permits the distal tip portion of the guide catheter 110 to align substantially coaxially within the ostium 157 and lumen of the left main coronary artery 154 as shown in FIG. 8C. Third, this configuration maximizes the stability and "backup support" achieved by the substantially contiguous contact portion (against the wall of the ascending aorta 158) because the axis of support of guide catheter 110 (provided primarily by the third straight portion 134 and fourth straight portion 138) substantially directly opposes the axis of stenotic "push back" forces as shown in FIG. 8D. In addition, the mild bend (an obtuse angle of about 160°, or between 140° to 160°) of the primary curve portion 137 of the guide catheter 110 further facilitates the transmission of pushing forces from the proximal end to the distal end of the balloon catheter because of the lack of acute or sharp 90° angles in the distal end portion of the guide catheter 110 when fully disposed in the aortic complex (FIG. 8C). The effects of this configuration increase the probability of the balloon catheter crossing a tight stenosis without prolapse of the guide catheter 110.

In addition, several advantages of the distal tip portion combination of the guide catheter 110 result from the fourth straight portion 138 being relatively long, preferably longer than the third straight portion 134. First, this causes the apex of the primary curve portion 137 to be outside the ostium 157 preferably halfway between the ascending aortic wall and the ostium. This allows only the fourth straight portion 138 to be intubated within the ostium 157 (of the LMCA). Because no part of the primary curve portion 137 nor the third straight portion 134 is within the ostium 157, and because of the mildness of the obtuse angle of the primary curve portion 137, the fourth straight portion 138 can be truly coaxially intubated within the ostium 157. Moreover, because the fourth straight portion 138 is longer than the third straight portion 134, the ostium 157 can be intubated coaxially much deeper then a guide catheter with a short straight portion (distal of the primary curve) because the primary curve portion of the guide catheter 110 does not obstruct deep intubation. Moreover, the ability of the fourth straight portion 138 to deeply intubate further accentuates coaxially positioning because as the fourth straight portion 138 is deeper within the ostium 157, this increases the surface contact between an outer surface of the wall of the guide catheter 110 and the surface of the wall of the ostium 157. This increased surface area contact tends to straighten the fourth straight portion 138 within the ostium so that it becomes increasingly coaxially positioned as the fourth straight portion 138 is intubated further within the ostium.

Another advantage of the long fourth straight portion 138 (longer than the straight portion just distal to the secondary curve portion) associated with keeping the apex of the primary curve portion 137 outside the ostium 157 is that the apex of the primary curve portion 137 is not leveraged against (i.e., banked) the wall of the ostium 157. This decreases the risk of injuring the ostia wall because of localized pressure against the wall. Finally, because the fourth straight portion 138 is relatively long, this allows the combination of the third straight portion 134, primary curve portion 137 and fourth straight portion 138 to form the generally rectilinearly axis of support across the ascending aorta.

Another advantage of the guide catheter 110 is that the orientation of the guide catheter 110 as shown in FIG. 8C can be achieved despite anatomical variations from person to person (except cases of gross malformation). Anatomical variations between persons relate primarily to variations in the size, shape and in particular, circumference of the lumen. For example, the lumen of the ascending aorta 158 may be narrower than normal or broader than normal (dilated). Moreover, although the wall of the ascending aorta 158 may have more curvature in a dilated aorta, this too is a minor anatomical variation.

The pre-insertion (relaxed state) configuration of the guide catheter 110 is constructed to interact with an ascending aorta 158 despite the normal variations in the aorta (aside from cases of gross malformation). In particular, the second straight portion 124 and the proximal portion of the secondary curved portion 130 of the distal end portion together provide a contact portion for resting substantially contiguously against the wall of the ascending aorta 158. This remains true despite variations in the size of the ascending aorta 158. To account for aortic size variations, a physician need only choose an appropriate size catheter just as would be done when using conventional catheters. For instance, a 3.5 distal tip size catheter would be used for a narrow aorta, a 4.0 distal tip size would be used for a normal aorta, and a 4.5 (or 5.0, 6.0) distal tip size guide catheter would be used for a dilated aorta. The distal tip size corresponds to the distance between the distal end of the guide catheter and the apex of the secondary curve portion. Moreover, in addition to having different size guide catheters to account for aortic size variations, to the extent that an aorta varies in size/shape, the secondary curved portion 130 readily accommodates this change so that the contact portion (including the second straight portion 124 and the proximal portion 131 of the secondary curved portion 130) remains in contact with the ascending aortic wall in a substantially contiguous manner.

The physician also can choose a catheter of the present invention with slightly different angles within the bounds of the invention to accommodate anatomical variations. For example, the obtuse angle of the tertiary curve portion 130 can be an angle in the range of 130° to 150°. Thus, if a more open angle tertiary curve portion 130 is required for the second straight portion 124 to rest substantially contiguous against the ascending aortic wall, then the physician can choose a guide catheter 110 off the shelf having a tertiary curve portion 123 with a 150° obtuse angle. Similarly, guide catheters of the present invention can be constructed so that in all cases, the tertiary curve portion will permit a contact portion to rest substantially contiguous against the wall of the ascending aorta and allow a distal end of the contact portion to be positioned substantially directly across from the ostium.

Next, several additional embodiments of the present invention are presented and provide examples of variations on dimensions of the curve portions and straight portion segments of the guide catheter 110. The variations relate primarily to selective increases in length of the straight portions. The variations in dimension provide catheters with a different distal tip size and different second straight portion size to accommodate different patient anatomies so that the substantially contiguous contact portion and low point o support can be established against the ascending aortic wall despite anatomical variations. In general, the guide catheters with smaller distal tip sizes and second straight portion lengths accommodate narrower and normal aortic roots, whereas the longer distal tip sizes (and second straight portions) accommodate dilated (wider) aortic roots. All the features of additional embodiments are the same as for the guide catheter 110 except for the specific changes in length of the straight portion segments. All of these additional embodiments enjoy the advantages of the guide catheter 110 that result from its unique combination of curve portions (including the tertiary curve portion 123) and optimal length straight segments.

Figure 9:
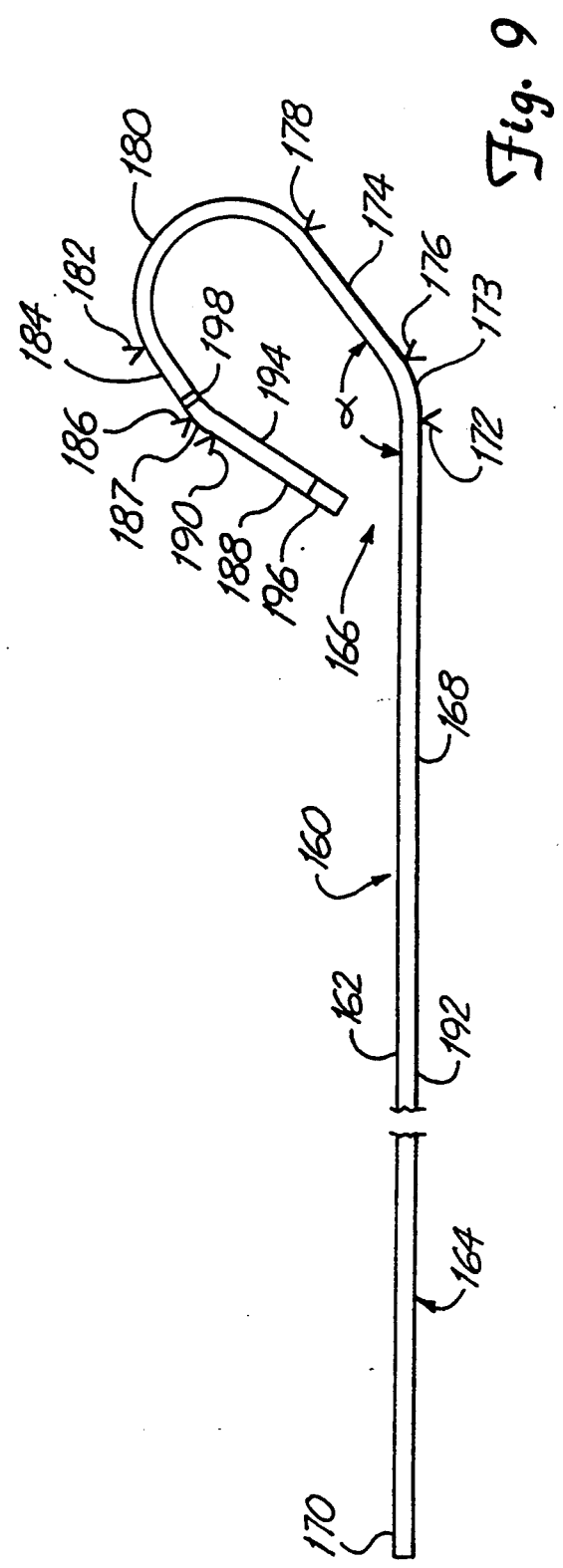
FIG. 9 is a plan view of a guiding catheter of the present invention.

Another embodiment of the present invention is a guide catheter 160 illustrated in FIG. 9 in its relaxed state prior to insertion in a cardiovascular system. The guide catheter 160 includes a shaft 162 extending from a proximal portion 164 to a distal portion 166. A first straight portion 168 of the guide catheter 160 extends rectilinearly from a proximal end 170 of the catheter 160 to a point 172 located distally along the catheter shaft 162. A tertiary curve portion 173 of the guide catheter 160 is defined by the curvature of the obtuse angle α (about 140°) of the catheter shaft 162 between the point 172 and a point 176 located distally along the shaft 162. The obtuse angle of the tertiary curve portion 173 can be between 130° and 150°. A second straight portion 174 of the guide catheter 160 extends rectilinearly and distally about 1.5 centimeters from the point 176 to a point 178. A secondary curved portion 180 of guide catheter 160 extends distally from the point 178 to point 182 forming an arc of approximately 180°. The curvature of the secondary curve portion 180 can form an arc of between 150° to 180° if desired. A third straight portion 184 of the guide catheter 160 extends rectilinearly about 0.75 centimeters between a point 182 and a point 186 located distally along catheter shaft 162. A primary curve portion 187 of guide catheter 160 is defined by the curvature of the catheter 160 from the point 186 to a point 190 located distally along the shaft 162. The obtuse angle of the primary curve portion 187 is about 160° as shown in FIG. 9 but can be between 140° to 160°. A fourth straight portion 188 of the guide catheter 162 extends distally and rectilinearly about 1.75 centimeters from the point 190 on the shaft 162.

The guide catheter 160 is inserted into the cardiovascular system in the manner previously described for guide catheter 110 and as depicted in FIGS. 8A–8D. The guide catheter 160 assumes the same advantageous orientation within the ascending aorta and ostium of the left main coronary artery as is shown in FIG. 8C (as shown for the guide catheter 110). As shown in FIG. 9 the guide catheter 162 is constructed of three segments, each with a different degree of flexibility. The guide catheter 160 in FIG. 9 has a first flexibility segment 192 with a Shore D hardness of 63, a second flexibility segment 194 with a Shore D hardness of 40, and a third flexibility tip segment 196 with a Shore D hardness of about 35. A bond ring member 198 is sandwiched between a distal end of the first segment 192 and a proximal end of the second segment 194, and has a hardness of about 51.

Instead of the triple flexibility segment construction, the guide catheter 160 can have a double flexibility segment construction as described for the guide catheter 110. In addition, for both the double and triple flexibility segment constructions of the guide catheter 160, the materials of PEBAX ®, TEFLON ®, and wire braiding are used as was described for the guide catheter 110.

The guide catheter 160 has a distal tip size 3.5 which corresponds to a distance of 3.5 centimeters between the utmost distal end of the guide catheter shaft 162 and the apex of the secondary curve portion 180. This distal tip size is used to accommodate slightly narrow or normal size aortic root anatomies.

Figure 10:
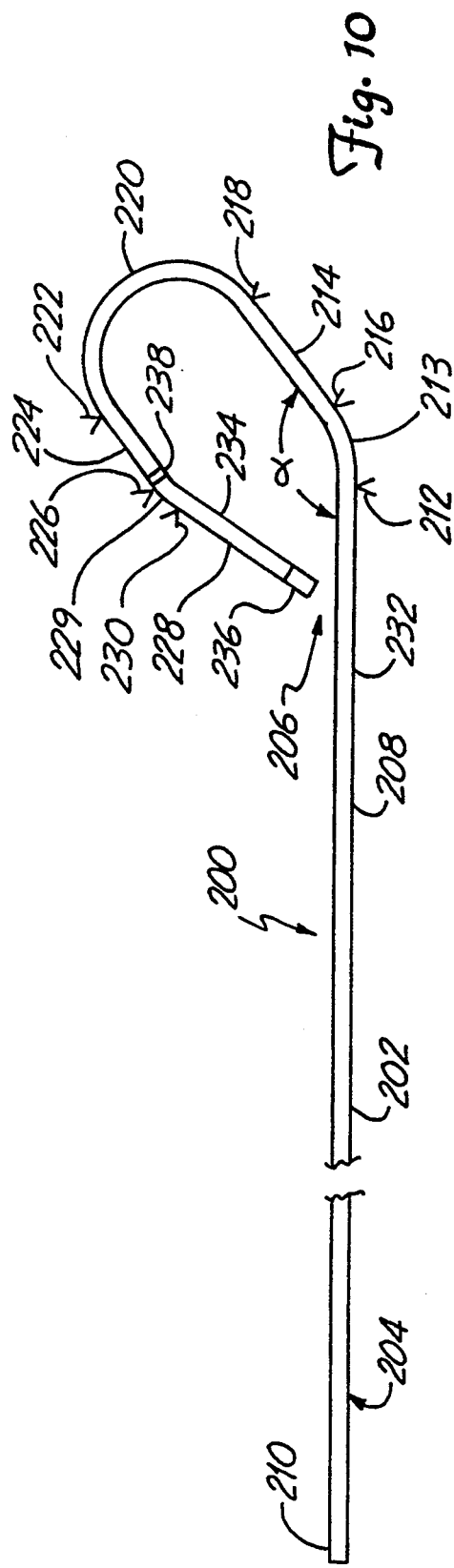
FIG. 10 is a plan view of a guiding catheter of the present invention.

Another embodiment of the present invention, a guide catheter 200, as shown in FIG. 10 includes a shaft 202 extending from a proximal portion 204 to a distal portion 206. A first straight portion 208 of the guide catheter 200 extends about 90–95 centimeters from a proximal end 210 to a point 212 located distally along the catheter shaft 202. A tertiary curve portion 213 of the guide catheter 200 is defined by the curvature of the catheter shaft 202 extending from the point 212 to a point 216 located distally along the shaft 202. The tertiary curve portion 213 has an obtuse angle α of about 140° as shown in FIG. 10 but can be between 130° to 150°. A second straight portion 214 of the guide catheter 200 extends distally and rectilinearly about 1.5 centimeters from the point 216 to a point 218 located distally along the shaft 202. A secondary curved portion 220 of the catheter 200 is defined by the curvature of the guide catheter shaft 202 extending in an approximately 180° arc from point 218 to a point 222 located distally along the catheter shaft 202. A third straight portion 224 of the guide catheter 200 extends distally and rectilinearly about 1 centimeter from the point 222 to a point 226 located distally along the catheter shaft 202. A fourth straight portion 228 of the guide catheter 200 extends distally and rectilinearly about 2 centimeters from a point 230 located just distally of the point 226. A primary curve portion 229 of the guide catheter 200 is defined by the curvature in the catheter shaft 202 formed between the third straight portion 224 and the fourth straight portion 228. The obtuse angle of the primary curve portion 229 is about 160° as shown in FIG. 10 but can be between about 140° to 160°.

The guide catheter 200 is inserted into the cardiovascular system in the manner previously described for guide catheter 110 and as depicted in FIGS. 8A–8D. The guide catheter 200 assumes the same advantageous orientation within the ascending aorta and ostium of the left main coronary artery as is shown in FIG. 8C (as shown for the guide catheter 110). As shown in FIG. 10 the guide catheter 200 is constructed of three segments, each with a different degree of flexibility. The guide catheter 200 in FIG. 10 has a first flexibility segment 232 with a Shore D hardness of 63, a second flexibility segment 234 with a Shore D hardness of 40, and a third flexibility tip segment 236 with a Shore D hardness of about 35. A bond ring member 238 is sandwiched between a distal end of the first segment 232 and a proximal end of the second segment 234, and has a hardness of about 51.

Instead of the triple flexibility segment construction, the guide catheter 200 can have a double flexibility segment construction as described for the guide catheter 110. In addition, for both the double and triple flexibility segment constructions of the guide catheter 200, the materials of PEBAX®, TEFLON®, and wire braiding are used as was described for the guide catheter 110.

The guide catheter 200 has a distal tip size 4.0 which corresponds to a distance of 4.0 centimeters between the utmost distal end of the guide catheter shaft 202 and the apex of the secondary curve portion 220. This 4.0 distal tip size is primarily used in normal or average size ascending aortic roots.

Another embodiment of the present invention is a guide catheter 240 which is shown in FIG. 11 in a relaxed state prior to insertion in the cardiovascular system. The guide catheter 240 includes a shaft 242 extending from a proximal portion 244 to a distal portion 246. A first straight portion 248 of the guide catheter 240 extends distally about 90 to 95 centimeters from a proximal end 250 to a point 252 located distally along the catheter shaft 242. A tertiary curve portion 253 is defined by the curvature of the catheter shaft 242 extending distally from the point 252 to a point 256 located distally therefrom. The tertiary curve portion 253 forms an obtuse angle α of about 140° as shown in FIG. 11 but can be between 130° to 150°. A second straight portion 254 of the guide catheter 240 extends distally and rectilinearly about 2 centimeters from the point 256 to a point 258 located distally along the catheter shaft 242. A secondary curve portion 260 of the guide catheter 240 is defined by the curvature of the catheter shaft 242 extending distally from the point 258 to a point 262 located distally along the catheter shaft 242. The secondary curve portion 260 as shown in FIG. 11 forms an arc of about 180° but can have an arc of about between 150° to 180°. A third straight portion 264 of the guide catheter 240 extends distally and rectilinearly about 1.25 centimeters from the point 262 to a point 266 located distally along the catheter shaft 242. A primary curve portion 269 of the guide catheter 240 is defined by the curvature of the catheter shaft 242 between the point 266 and a point 270 located distally therefrom along the catheter shaft 242. The primary curve portion 269 forms an obtuse angle of about 160° as shown in FIG. 11 but can be between about 140° to 160°. A fourth straight portion 268 of the guide catheter 240 extends rectilinearly about 2.25 centimeters distally from the point 270.

The guide catheter 240 is inserted into the cardiovascular system in the manner previously described for guide catheter 110 and as depicted in FIGS. 8A–8D. The guide catheter 240 assumes the same advantageous orientation within the ascending aorta and ostium of the left main coronary artery as is shown in FIG. 8C (as shown for the guide catheter 110). As shown in FIG. 11 the guide catheter 240 is constructed of three segments, each with a different degree of flexibility. The guide catheter 240 in FIG. 11 has a first flexibility segment 272 with a Shore D hardness of 63, a second flexibility segment 274 with a Shore D hardness of 40, and a third flexibility tip segment 276 with a Shore D hardness of about 40, and a third flexibility tip segment 276 with a Shore A hardness of about 35. A bond ring member 278 is sandwiched between a distal end of the first segment 272 and a proximal end of the second segment 274, and has a hardness of about 51.

Instead of the triple flexibility segment construction, the guide catheter 240 can have a double flexibility segment construction as described for the guide catheter 110. In addition, for both the double and triple flexibility segment constructions of the guide catheter 240, the materials of PEBAX®, TEFLON®, and wire braiding are used as was described for the guide catheter 110.

The guide catheter 240 has a distal tip size 4.5 which corresponds to a distance of 4.5 centimeters between the utmost distal end of the guide catheter shaft 242 and the apex of the secondary curve portion 260.

Another embodiment of the present invention, a guide catheter 280, is shown in FIG. 12 in a relaxed state prior to insertion in the cardiovascular system. The guide catheter 280 includes a shaft 282 extending from a proximal portion 284 to a distal portion 286. A first straight portion 288 of the guide catheter 280 extends about 90 to 95 centimeters from a proximal end 290 to a point 292 located distally along the catheter shaft 282. A tertiary curve portion 293 of the guide catheter 280 is defined by the curvature of the catheter shaft 282 from the point 292 to a point 296 located distally therefrom. The tertiary curve portion 293 forms an obtuse angle α of about 140° as shown in FIG. 12 but can be between about 130° to 150°. A second straight portion 294 of the guide catheter 280 extends distally and rectilinearly about 2.5 centimeters from the point 296 to a point 298 located distally along the catheter shaft 282. A secondary curve portion 300 of the guide catheter 280 extends distally from the second straight portion 244 and is defined by the curvature of the catheter shaft 282 forming an arc of about 180° (as shown in FIG. 12) between the point 298 and a point 302 located distally therefrom. The secondary curve portion 300 can have an arc of between 150° to 180°. A third straight portion 304 of the guide catheter 280 extends distally and rectilinearly about 1.5 centimeters from the point 302 to a point 306 located distally therefrom along the catheter shaft 282. A primary curve portion 307 of the guide catheter 280 is defined by the curvature of the catheter shaft 282 between the point 306 and a point 308 extending distally therefrom. The primary curve portion 307 as shown in FIG. 12 forms an obtuse angle of about 160° but that obtuse angle can be between 140° to 160°. A fourth straight portion 310 of the guide catheter 280 extends distally from the point 308 and rectilinearly about 2.5 centimeters.

The guide catheter 280 is inserted into the cardiovascular system in the manner previously described for guide catheter 110 and as depicted in FIGS. 8A–8D. The guide catheter 280 assumes the same advantageous orientation within the ascending aorta and ostium of the left main coronary artery as shown in FIG. 8C (as shown for the guide catheter 110). As shown in FIG. 12 the guide catheter 280 is constructed of three segments, each with a different degree of flexibility. The guide catheter 280 in FIG. 12 has a first flexibility segment 312 with a Shore D hardness of 63, a second flexibility segment 314 with a Shore D hardness of 40, and a third flexibility tip segment 316 with a Shore D hardness of about 35. A bond ring member 318 is sandwiched between a distal end of the first segment 232 and a proximal end of the second segment 314, and has a hardness of about 51.

Instead of the triple flexibility segment construction, the guide catheter 280 can have a double flexibility segment construction as described for the guide catheter 110. In addition, for both the double and triple flexibility segment constructions of the guide catheter 280, the materials of PEBAX®, TEFLON®, and wire braiding are used as was described for the guide catheter 110.

The guide catheter 280 has a distal tip size 5.0 which corresponds to a distance of 5.0 centimeters between the utmost distal end of the guide catheter shaft 282 and the apex of the secondary curve portion 300. This 5.0 distal tip size with the longer second straight portion is designed to accommodate larger size and dilated ascending aortic roots.

Another embodiment of the present invention, a guide catheter 320, is shown in FIG. 13 in a relaxed state prior to insertion in the cardiovascular system. The guide catheter 320 has a shaft 322 extending from a proximal portion 324 to a distal portion 326. A first straight portion 328 of the guide catheter 320 extends about 90 to 95 centimeters distally from a proximal end 330 to a point 332 located distally along the catheter shaft 322. A tertiary curve portion 333 of the guide catheter 320 is defined by the curvature of the catheter shaft 322 between the point 332 and a point 336 located distally therefrom. The tertiary curve portion 333 forms an obtuse angle α of about 140° as shown in FIG. 13 but can be between 130° to 150°. A second straight portion 334 of the guide catheter 320 extends rectilinearly about 2.5 centimeters and distally from the point 336 to a point 338 located distally along the catheter shaft 322. A secondary curve portion 340 of the guide catheter 320 is defined by the curvature of the catheter shaft 322 extending distally from the point 338 to a point 342 located distally along the catheter shaft 322 and forming an arc of approximately 180° as shown in FIG. 13. The arc of the secondary curve portion 340 can be between 150° to 180°. A third straight portion 344 of the guide catheter 320 extends distally and rectilinearly about 2 centimeters from the point 342 to a point 346 located distally therefrom along the catheter shaft 322. A primary curve portion 347 of the guide catheter 320 is defined by the curvature of the catheter 322 extending distally from the point 346 to a point 350. As shown in FIG. 13, the primary curve portion 347 forms an obtuse angle of about 160° but this angle can be between 140° and 160°. A fourth straight portion 348 of the guide catheter 320 extends about 3 centimeters distally and rectilinearly from the point 350 to form a tip portion of the catheter 320. As shown in FIG. 13, the fourth straight portion 348 overlaps with the first straight portion 328 such that the fourth straight portion 348 extends in a plane different than that of the first straight portion 328.

The guide catheter 320 is inserted into the cardiovascular system in the manner previously described for guide catheter 110 and as depicted in FIGS. 8A–8D. The guide catheter 320 assumes the same advantageous orientation within the ascending aorta and ostium of the left main coronary artery as shown in FIG. 8C (as shown for the guide catheter 110). As shown in FIG. 13 the guide catheter 320 is constructed of three segments, each with a different degree of flexibility. The guide catheter 320 in FIG. 13 has a first flexibility segment 352 with a Shore D hardness of 63, a second flexibility segment 354 with a Shore D hardness of 40, and a third flexibility tip segment 356 with a Shore D hardness of about 35. A bond ring member 358 is sandwiched between a distal end of the first segment 352 and a proximal end of the second segment 354, and has a hardness of about 51.

Instead of the triple flexibility segment construction, the guide catheter 320 can have a double flexibility segment construction as described for the guide catheter 110. In addition, for both the double and triple flexibility segment constructions of the guide catheter 320, the materials of PEBAX®, TEFLON®, and wire braiding are used as was described for the guide catheter 110.

The guide catheter 320 has a distal tip size 6.0 which corresponds to a distance of 6.0 centimeters between the utmost distal end of the guide catheter shaft 322 and the apex of the secondary curve portion 340. This 6.0 distal tip size is provided for large and dilated aortic roots.

The guide catheters of the present invention, yield many advantages over previous prior art guide catheters (such as the Judkins-style guiding catheter) in connection with the goal of catheterization of the left main coronary artery. These guide catheters of the present invention have an overall configuration or basic shape that is substantially different than a Judkins-style guide catheter. Accordingly, when the guide catheters of the present invention are deployed in the cardiovascular system (as in FIG. 8C), an orientation is achieved within the ascending aorta and ostium of the left main coronary artery that is superior (i.e., better) than the corresponding orientation achieved by a Judkins-style guide catheter.

The primary feature of superior (i.e., better) orientation of the guide catheters of the present invention is that, when disposed in the aortic complex, a contact portion of the guide catheter is established in a substantially contiguous manner against the aortic wall for a substantial length (at least about 1.5 centimeters). Moreover, a distal end of this contact portion is positioned against the aortic wall substantially directly opposite the ostium of the left main coronary artery. This provides a primary point of backup support for the guide catheter that directly opposes stenotic pushback forces directed outwardly from the ostium of the left main coronary artery. In addition, a distal tip portion of the guide catheters of the present invention (including the third and fourth straight portions) when disposed in the aortic complex provide a generally rectilinear axis of support that extends substantially across the ascending aorta from the distal end of the contact portion to the ostium of the left main coronary artery. This axis of support substantially directly opposes the axis of the stenotic push back forces (FIG. 8D), thereby substantially diminishing the potential for prolapse of the distal tip portion of the guide catheters of the present invention. Furthermore, the guide catheter lumen at the distal tip is aligned essentially coaxially with the lumen of the left main coronary artery.

This advantageous orientation of the guide catheters of the present invention (when in the aortic complex) result directly from the configuration of the guide catheters when in a relaxed state prior to insertion in the cardiovascular system. Foremost, the guide catheters of the present invention have a transition portion including a tertiary curve portion and a second straight portion positioned between a first straight portion and a secondary curve portion. The transition portion forms an obtuse angle of between 130° to 150°. This transition portion causes the second straight portion and a proximal portion of the secondary curve portion to form the contact portion (in use) that rests substantially contiguous against the wall of the ascending aorta. The presence of the transition portion causes the second straight portion to rest naturally against the ascending aortic wall thereby allowing the primary point of backup support (a distal end of the contact portion) to be positioned very low in the ascending aorta as compared to the single point of backup support for a Judkins-style catheter. The primary point of backup support for the guide catheters of the present invention is a point along the ascending aortic wall substantially directly opposite the ostium of the left main coronary artery. Moreover, because the second straight portion of the guide catheter of the present invention rests naturally against the ascending aortic wall, a large area of general backup support is provided for the guide catheter which makes it quite difficult to dislodge the guide catheter from its desired orientation.

In addition, the presence of the tertiary curve portion provides more bends in the guide catheter (than a Judkins-style guide catheter) when disposed in the aortic complex thereby making each bend in the catheter a milder angle to allow a fuller transmission of distal pushing forces through the guide catheter. Moreover, the mild obtuse angle (about 160°) of the primary curve portion of the guide catheter and the long fourth straight portion (preferably longer than the third straight portion) cause the distal tip portion to align substantially coaxially within the ostium of the left main coronary artery. The long fourth straight portion also maintains the primary curve portion within the ascending aorta outside of the ostium of the left main coronary artery.

Although the present invention has been described with reference to preferred embodiments, workers skilled in the art will recognize that changes may be made in form and detail without departing from the spirit and scope of the invention.

It is understood that several variations may be made in the guide catheters of the present invention without departing from the scope of the invention. For example, the catheters embodied in the present invention are not limited for use as guiding catheters but can have other uses for treatment of the cardiovascular system, such as use as diagnostic, balloon, laser and atherectomy catheters, etc. Also, the specific lengths and angles of the specific examples of the catheters of the present invention set forth above can be varied within the scope of the invention. Moreover, it is understood that, instead of the well defined lengths and angles shown and described in the above examples, the distal end portion of the catheters of the present invention can form more smoother curves within the scope of the invention.

What is claimed is:

1. A femoral approach angioplasty guide catheter adapted for selective catheterization of a left main coronary artery within a cardiovascular system comprising:
   an elongate flexible tubular member in a relaxed state prior to insertion in the cardiovascular system further comprising in consecutive arrangement:
   a first straight proximal portion extending distally from a proximal end of the tubular member;
   a second straight portion joined to the first straight portion and having a length of about 1.5 to 2.5 centimeters;
   a tertiary curved portion defining a junction of the first straight portion and the second straight portion and defining a vertex of an obtuse angle of 130° to 150° between the first and second straight portions;
   a secondary curved portion joined to the second straight portion and having an arcuate curvature of about 150° to 180° and a radius of curvature of about 1 centimeter;
   a third straight portion joined to the secondary curved portion;
   a fourth straight portion joined to the third straight portion and having a distal end defining a terminal distal tip of the tubular member; and
   a primary curved portion a junction of the third straight portion and the fourth straight portion and defining a vertex of an obtuse angle of 140° to 160° between the third and fourth straight portions,
   wherein the interiors of the tertiary curved portion and every curve portion distal thereof, including the secondary curved portion and the primary curved portion, all generally face each other,
   wherein the first straight portion, second straight portion, third straight portion, and fourth straight portion all lie in generally the same plane, the third straight portion and the fourth straight portion extending slightly out of plane to the extent that the fourth straight portion overlaps the first straight portion, and wherein the length of the fourth straight portion is approximately equal to the sum of the length of the third straight portion and the radius of curvature of the secondary curved portion.

2. The catheter of claim 1 wherein:
the second straight portion has a length of about 1.5 centimeters, the third straight portion has a length of about 0.5 to 1.0 centimeters, and the fourth straight portion has a length of about 1.5 to 2.0 centimeters.

3. The catheter of claim 1 wherein:
the second straight portion has a length of about 2.0 centimeters, the third straight portion has a length of about 1.25 centimeters, and the fourth straight portion has a length of about 2.25 centimeters.

4. The catheter of claim 1 wherein:
the second straight portion has a length of about 2.5 centimeters, the third straight portion has a length of about 1.5 to 2.0 centimeters, and the fourth straight portion has a length of about 2.5 to 3.0 centimeters.

5. The catheter of claim 1 wherein the third straight portion has a length of about 0.5 to 2.0 centimeters.

6. The catheter of claim 1 wherein the fourth straight portion has a length of about 1.5 to 3.0 centimeters.

7. The catheter of claim 1 wherein the sum of the lengths of the fourth straight portion and third straight portion and the radius of curvature of the secondary curved portion is about 3.5 to 6.0 centimeters.

* * * * *